United States Patent
Kim et al.

(10) Patent No.: US 11,177,444 B2
(45) Date of Patent: Nov. 16, 2021

(54) ORGANIC ELECTROLUMINESCENT DEVICE

(71) Applicant: LG CHEM, LTD., Seoul (KR)

(72) Inventors: Dongheon Kim, Daejeon (KR); Kongkyeom Kim, Daejeon (KR); Hyungjin Lee, Daejeon (KR); Nansra Heo, Daejeon (KR); Woochul Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 455 days.

(21) Appl. No.: 16/303,638

(22) PCT Filed: Oct. 13, 2017

(86) PCT No.: PCT/KR2017/011335
§ 371 (c)(1),
(2) Date: Nov. 20, 2018

(87) PCT Pub. No.: WO2018/070840
PCT Pub. Date: Apr. 19, 2018

(65) Prior Publication Data
US 2020/0321534 A1    Oct. 8, 2020

(30) Foreign Application Priority Data
Oct. 14, 2016 (KR) .................. 10-2016-0133789

(51) Int. Cl.
*C07C 15/28* (2006.01)
*C07D 471/10* (2006.01)
(Continued)

(52) U.S. Cl.
CPC .......... *H01L 51/0072* (2013.01); *C07C 15/28* (2013.01); *C07D 251/24* (2013.01);
(Continued)

(58) Field of Classification Search
CPC .................................................. H01L 51/5024
See application file for complete search history.

(56) References Cited

U.S. PATENT DOCUMENTS 9,203,033 B2 * 12/2015 Park ....................... C09K 11/06
2001/0012572 A1    8/2001 Araki
(Continued)

FOREIGN PATENT DOCUMENTS

| CN | 105237324 A | 1/2016 |
| JP | 2013-084965 A | 5/2013 |

(Continued)

OTHER PUBLICATIONS

Computer-generated English-language translation of KR-20130039671-A.*

(Continued)

*Primary Examiner* — Vu A Nguyen
(74) *Attorney, Agent, or Firm* — Dentons US LLP

(57) ABSTRACT

The present specification relates to an organic electroluminescent device comprising: a first electrode; a second electrode; and an organic material layer provided between the first electrode and the second electrode, wherein the organic material layer comprises a light emitting layer and an electron transfer layer, the light emitting layer comprises a first host material, a second host material and a dopant material, the first host material has a HOMO energy level of −5.9 eV or lower, and the second host material has a HOMO energy level higher than a HOMO energy level of the first host material by 0.1 eV to 0.2 eV.

13 Claims, 3 Drawing Sheets

(51) Int. Cl.
  *C07D 251/24* (2006.01)
  *H01L 51/00* (2006.01)
  *H01L 51/50* (2006.01)
  *C07D 307/91* (2006.01)
  *C09K 11/06* (2006.01)

(52) U.S. Cl.
  CPC ......... *C07D 307/91* (2013.01); *C07D 471/10* (2013.01); *C09K 11/06* (2013.01); *H01L 51/0052* (2013.01); *H01L 51/0058* (2013.01); *H01L 51/0067* (2013.01); *H01L 51/0073* (2013.01); *C07C 2603/24* (2017.05); *C09K 2211/1018* (2013.01); *H01L 51/5012* (2013.01); *H01L 51/5016* (2013.01); *H01L 51/5072* (2013.01); *H01L 51/5088* (2013.01); *H01L 51/5092* (2013.01); *H01L 51/5096* (2013.01); *H01L 2251/5384* (2013.01); *H01L 2251/552* (2013.01)

(56) References Cited

U.S. PATENT DOCUMENTS

| | | | |
|---|---|---|---|
| 2013/0092909 A1 | 4/2013 | Han et al. | |
| 2015/0255741 A1 | 9/2015 | Lee et al. | |
| 2016/0087217 A1* | 3/2016 | Ito ................. | H01L 51/0073 257/40 |
| 2016/0197289 A1 | 7/2016 | Sado et al. | |
| 2017/0069864 A1 | 3/2017 | Lee et al. | |
| 2017/0279055 A1 | 9/2017 | Jang et al. | |
| 2018/0138417 A1 | 5/2018 | Ito et al. | |

FOREIGN PATENT DOCUMENTS

| | | | | |
|---|---|---|---|---|
| JP | 2015-018883 | A | | 1/2015 |
| KR | 10-2003-0032150 | A | | 4/2003 |
| KR | 10-2012-0015883 | A | | 2/2012 |
| KR | 10-2013-0039671 | A | | 4/2013 |
| KR | 20130039671 | A | * | 4/2013 |
| KR | 10-2015-0077587 | A | | 7/2015 |
| KR | 10-2015-0099750 | A | | 9/2015 |
| KR | 10-2015-0105520 | A | | 9/2015 |
| KR | 10-2015-0141271 | A | | 12/2015 |
| KR | 10-2016-0036160 | A | | 4/2016 |
| KR | 10-2016-0049500 | A | | 5/2016 |
| KR | 10-2016-0050614 | A | | 5/2016 |
| KR | 10-2016-0076461 | A | | 6/2016 |
| KR | 10-2017-0029708 | A | | 3/2017 |
| WO | WO-2015099413 | A1 | * | 7/2015 ......... H01L 51/5016 |

OTHER PUBLICATIONS

Computer-generated English-language translation of WO-2015099413-A1.*
SciFinder Search. (Year: 2021).*
Ju-An Yoon et al., "Highly efficient blue organic light-emitting diodes using quantum well-llke multiple emissive layer structure", Nanoscale Research Letters, 2014, vols. 191, pp. 1-7.

* cited by examiner

[FIG. 1]
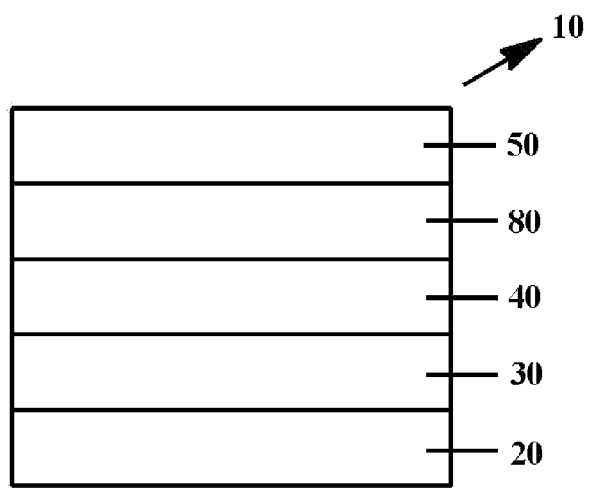

[FIG. 2]
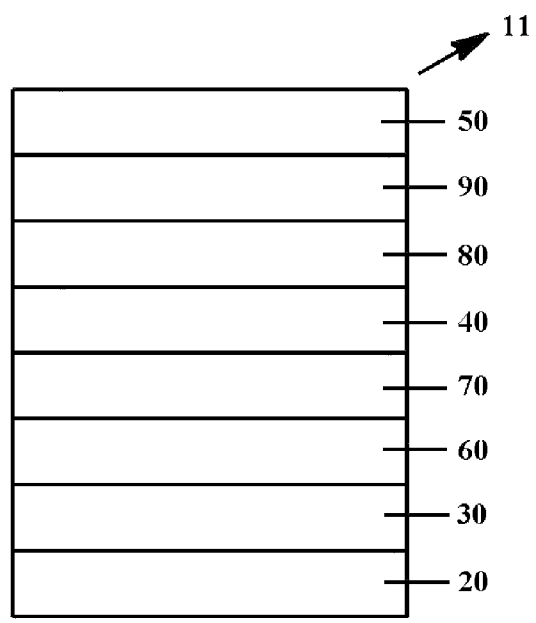

[FIG. 3]
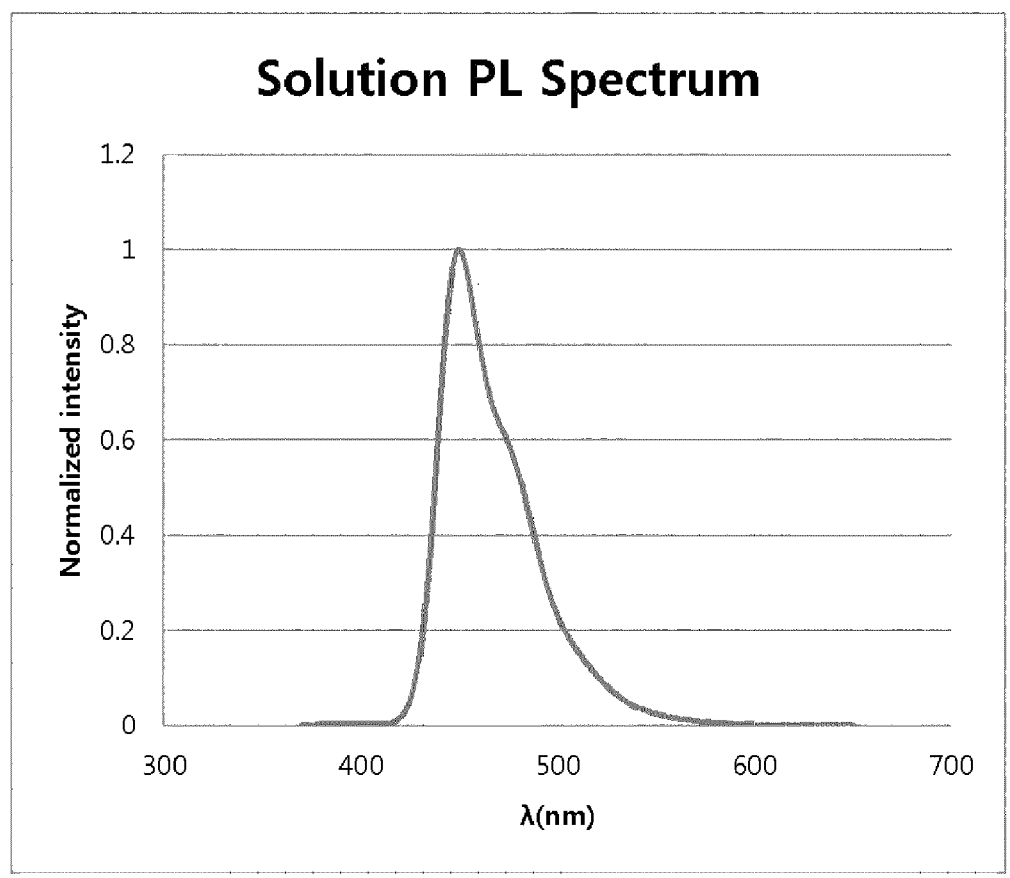

ORGANIC ELECTROLUMINESCENT DEVICE

TECHNICAL FIELD

This application is a National Stage Application of International Application No. PCT/KR2017/011335 filed Oct. 13, 2017, and claims the benefit of Korean Patent Application No. 10-2016-0133789 filed Oct. 14, 2016, all of which are hereby incorporated by reference in their entirety for all purposes as if fully set forth herein.

The present specification relates to an organic electroluminescent device.

BACKGROUND ART

An organic light emission phenomenon generally refers to a phenomenon converting electrical energy to light energy using an organic material. An organic electroluminescent device using an organic light emission phenomenon normally has a structure including an anode, a cathode, and an organic material layer therebetween. Herein, the organic material layer is often formed in a multilayer structure formed with different materials in order to increase efficiency and stability of the organic electroluminescent device, and for example, may be formed with a hole injection layer, a hole transfer layer, a light emitting layer, an electron transfer layer, an electron injection layer and the like. When a voltage is applied between the two electrodes in such an organic electroluminescent device structure, holes and electrons are injected to the organic material layer from the anode and the cathode, respectively, and when the injected holes and electrons meet, excitons are formed, and light emits when these excitons fall back to the ground state.

Development of new materials for such an organic electroluminescent device has been continuously required.

DISCLOSURE

Technical Problem

The present specification is directed to providing an organic electroluminescent device having a novel structure.

Technical Solution

One embodiment of the present specification provides an organic electroluminescent device comprising a first electrode; a second electrode; and an organic material layer provided between the first electrode and the second electrode, wherein the organic material layer comprises a light emitting layer and an electron transfer layer, the light emitting layer comprises a first host material, a second host material and a dopant material, the first host material has a HOMO energy level of −5.9 eV or lower, and the second host material has a HOMO energy level higher than a HOMO energy level of the first host material by 0.1 eV to 0.2 eV.

In addition, according to another embodiment of the present specification, the electron transfer layer comprises a compound represented by the following Chemical Formula 1 or Chemical Formula 2:

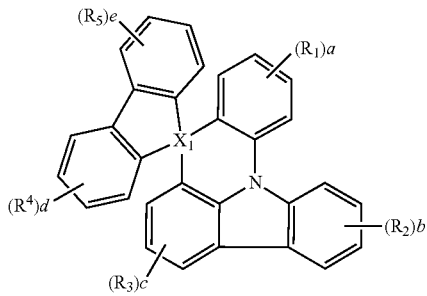

[Chemical Formula 1]

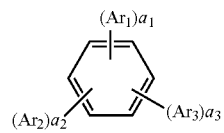

[Chemical Formula 2]

in Chemical Formulae 1 and 2, $X_1$ is C or Si, at least one of $R_1$ to $R_5$ is each independently represented by $-(L_1)z_1-A_1$, at least one of $Ar_1$ to $Ar_3$ is each independently represented by $-(L_2)z_2-A_2$, $a_1$ to $a_3$ are the same as or different from each other, and each independently an integer of 1 to 4, $a_1+a_2+a_3 \leq 6$, and when $a_1$ to $a_3$ are an integer of 2 or greater, substituents in the parentheses are the same as or different from each other, $L_1$ and $L_2$ are the same as or different from each other, and each independently a direct bond; or a divalent group comprising one or more types selected from the group consisting of a substituted or unsubstituted arylene group and a substituted or unsubstituted heteroarylene group, $z_1$ and $z_2$ are an integer of 1 or 2, and when $z_1$ and $z_2$ are 2, substituents in the parentheses are the same as or different from each other, $A_1$ and $A_2$ are the same as or different from each other, and each independently a substituted or unsubstituted aryl group; or a substituted or unsubstituted heteroaryl group comprising one or more Ns, the rest of $R_1$ to $R_5$ that are not $-(L_1)z_1-A_1$ and the rest of $Ar_1$ to $Ar_3$ that are not $-(L_2)z_2-A_2$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, a, b, d and e are the same as or different from each other, and each independently an integer of 1 to 4, c is an integer of 1 to 3, and when a to e are each 2 or greater, substituents in the parentheses are the same as or different from each other.

In addition, according to one embodiment of the present specification, at least one of the first host material and the second host material is represented by a compound of the following Chemical Formula 3:

[Chemical Formula 3]

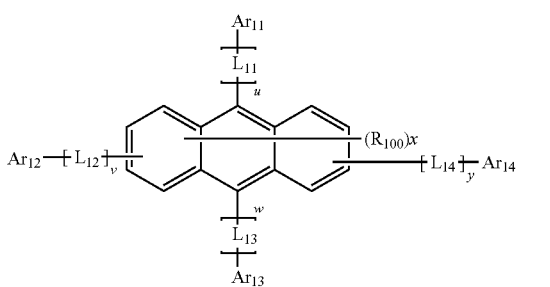

in Chemical Formula 3, $R_{100}$ is hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroaryl group, x is an integer of 1 to 6, and when x is 2 or greater, $R_{100}$s are the same as or different from each other, $L_{11}$ to $L_{14}$ are the same as or different from each other, and each independently a direct bond; or a substituted or unsubstituted arylene group, u, v, w and y are each an integer of 1 or 2, and when u is 2, $L_{11}$s are the same as or different from each other, when v is 2, $L_{12}$s are the same as or different from each other, when w is 2, $L_{13}$s are the same as or different from each other, and when y is 2, $L_{14}$s are the same as or different from each other, $Ar_{11}$ and $Ar_{13}$ are the same as or different from each other, and each independently a substituted or unsubstituted aryl group; or a substituted or unsubstituted heteroaryl group, and $Ar_{12}$ and $Ar_{14}$ are the same as or different from each other, and each independently hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroaryl group.

Advantageous Effects

An organic electroluminescent device according to one embodiment of the present specification can secure enhanced efficiency and/or low driving voltage by enhancing properties of hole injection from a hole transfer layer to a light emitting layer through co-depositing a first host material having a low HOMO energy level and a second host material having a relatively higher HOMO energy level in a specific ratio as the light emitting layer.

Moreover, a lifetime property can be enhanced by using an electron transfer layer in a form of an electron donor and an electron acceptor bonding to each other.

DESCRIPTION OF DRAWINGS

FIG. 1 illustrates an organic electroluminescent device (10) according to one embodiment of the present specification.

FIG. 2 illustrates an organic electroluminescent device (11) according to another embodiment of the present specification.

FIG. 3 is a graph presenting a PL spectrum of a pyrene-based dopant material that may be used in the present specification.

REFERENCE NUMERAL 10, 11: Organic Electroluminescent Device
20: Substrate
30: First Electrode
40: Light Emitting Layer
50: Second Electrode
60: Hole Injection Layer
70: Hole Transfer Layer
80: Electron Transfer Layer
90: Electron Injection Layer

MODE FOR DISCLOSURE

Hereinafter, the present specification will be described in more detail.

According to one embodiment of the present specification, the light emitting layer comprises a first host material, a second host material and a dopant material, and the organic material layer may further comprise an electron transfer layer.

According to one embodiment of the present specification, the light emitting layer comprises a first host material and a second host material, the first host material and the second host material comprises a compound represented by Chemical Formula 3, the organic material layer may further comprise an electron transfer layer, and the electron transfer layer may comprise a compound represented by Chemical Formula 1 or Chemical Formula 2.

The first host material and the second host material according to one embodiment of the present specification have HOMO energy levels different from each other.

According to one embodiment of the present specification, the first host material may have a HOMO energy level of −5.9 eV or lower.

According to one embodiment of the present specification, the second host material may have a HOMO energy level higher than a HOMO energy level of the first host material by 0.1 eV to 0.2 eV. More specifically, the second host material may have a HOMO energy level higher than a HOMO energy level of the first host material by 0.1 eV to 0.15 eV.

In the present specification, an "energy level" means magnitude of energy. Accordingly, even when an energy level is expressed in a negative (−) direction from a vacuum level, the energy level is interpreted to mean an absolute value of the corresponding energy value. For example, having a deep energy level means an absolute value increasing in a negative direction from a vacuum level.

In the present specification, a HOMO energy level means energy difference from a vacuum level to a highest occupied molecular orbital. In addition, a LUMO energy level means energy difference from a vacuum level to a lowest unoccupied molecular orbital.

According to one embodiment of the present specification, the first host material having a HOMO energy level of −5.9 eV or lower means an energy level absolute value increasing in a negative direction from a vacuum level.

According to one embodiment of the present specification, the second host material having a HOMO energy level higher than a HOMO energy level of the first host material by 0.1 eV to 0.2 eV means having an energy level absolute value decreasing in a negative direction from the HOMO energy level of the first host material.

According to one embodiment of the present specification, the first host material has a HOMO energy level of −5.9 eV or lower, and the second host material has a HOMO energy level higher than a HOMO energy level of the first host material by 0.1 eV to 0.2 eV.

When the first host material and the second host material according to one embodiment of the present specification have HOMO energy levels in the above-mentioned ranges, a driving voltage is reduced and current efficiency is improved compared to using a host material having a deep HOMO energy level alone.

An organic electroluminescent device according to one embodiment of the present specification uses the first host material having a deep HOMO energy level, and the second host material having a HOMO energy level higher than a HOMO energy level of the first host material by 0.1 eV to 0.2 eV, and uses the compound represented by Chemical Formula 1 or Chemical Formula 2 as an electron transfer layer, and as a result, excellent performance is obtained in terms of a driving voltage, current efficiency and/or a lifetime.

Having a HOMO energy level of the second host material higher than a HOMO energy level of the first host material by greater than Δ0.2 eV or higher by less than Δ0.1 eV is disadvantageous in terms of current efficiency and/or a lifetime.

In the present specification, an "electron donor" is a side giving electrons when exchanging electron between atoms, molecules or ions.

In the present specification, an "electron acceptor" is a side receiving electrons from the other side when exchanging electron between atoms, molecules or ions.

In the present specification, a description of a certain part "comprising" certain constituents means capable of further including other constituents, and does not exclude other constituents unless particularly stated on the contrary.

In the present specification, a description of a certain member being placed "on" another member includes not only a case of the one member adjoining the another member but a case of still another member being present between the two members.

Examples of substituents in the present specification will be described below, however, the substituents are not limited thereto.

In the present specification, the term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one or more substituents selected from the group consisting of hydrogen; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, being substituted with a substituent linking two or more substituents among the substituents illustrated above, or having no substituents. For example, "a substituent linking two or more substituents" may be an aryl group substituted with an alkyl group, an aryl group substituted with an aryl group, an aryl group substituted with a silyl group, an aryl group substituted with a heteroaryl group, a heteroaryl group substituted with an alkyl group, a heteroaryl group substituted with an aryl group, a heteroaryl group substituted with a heteroaryl group, or the like.

In the present specification, the halogen group may be F, Cl, Br, I or the like.

In the present specification, the alkyl group may be linear or branched, and although not particularly limited thereto, the number of carbon atoms is preferably from 1 to 50. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl -2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the cycloalkyl group is not particularly limited, but preferably has 3 to 50 carbon atoms, and according to one embodiment, the number of carbon atoms of the cycloalkyl group is from 3 to 30. According to another embodiment, the number of the carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the aryl group is not particularly limited, but preferably has 6 to 50 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a fluoranthenyl group, a triphenylenyl group, a phenalenyl group, a chrysenyl group, a fluorenyl group, a benzofluorenyl group, a spirobifluorenyl group, a triphenylene group, a spirobenzoanthracenefluorenyl group and the like, but are not limited thereto.

In the present specification, the heteroaryl group is a group including one or more atoms that are not carbon, that is, heteroatoms, and specifically, the heteroatom may include one or more atoms selected from the group consisting of N, P, O, S, Se, Ge, Si and the like. The number of carbon atoms is not particularly limited, but is preferably from 2 to 50, and the heteroaryl group may be monocyclic or multicyclic. Examples of the heteroaryl group may include a thiophene group, a furanyl group, a pyrrole group, an imidazolyl group, a triazolyl group, an oxazolyl group, an isoxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a dibenzofuranyl group, a naphthobenzofuranyl group, a phenanthrolinyl group, a thiadiazolyl group, a phenothiazinyl group, acenaphthoquinoxalyl group, an indenoquinazolyl group, an indenoisoquinolyl group, an indenoquinolyl group, a pteridinyl group, a phenoxazinyl group, a benzoquinazolyl group, an indazolyl group, a benzoperimidinolyl group, a benzoperimidinyl group, a spiroacridinefluorenyl group and the like, but are not limited thereto.

In the present specification, the alkoxy group may be linear, branched or cyclic. The number of carbon atoms of the alkoxy group is not particularly limited, but is preferably from 1 to 50. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

In the present specification, the amine group may be selected from the group consisting of $-NH_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 50. Specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, an N-phenylnaphthylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, descriptions on the alkyl group provided above may be applied to the alkyl group in the alkylamine group, the alkylsilyl group, the alkylaryl group, the N-arylalkylamine group, the alkylthioxy group, the alkylsulfoxy group and the N-alkylheteroarylamine group.

In the present specification, descriptions on the heteroaryl group provided above may be applied to the examples of the heteroaryl group in the N-arylheteroarylamine group and the N-alkylheteroarylamine group.

In the present specification, the alkenyl group may be linear or branched, and although not particularly limited thereto, the number of carbon atoms is preferably from 2 to 50. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl -1-yl, 2-phenyl-2-(naphthyl-1-yl)vinyl-1-yl, 2,2-bis(diphenyl -1-yl)vinyl-1-yl, a stilbenyl group, a styrenyl group and the like, but are not limited thereto.

In the present specification, the silyl group may be represented by a chemical formula of —SiRaRbRc, and Ra, Rb and Rc may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by a chemical formula of —BRaRb, and Ra and Rb may each be hydrogen; a substituted or unsubstituted alkyl group; or a substituted or unsubstituted aryl group. Specific examples of the boron group may include a bimethylboron group, a biethylboron group, a t-butylmethylboron group, a biphenylboron group, a phenylboron group and the like, but are not limited thereto.

In the present specification, the fluorenyl group may be substituted, and adjacent groups may bond to each other to form a spiro structure.

When the fluorenyl group, the spirobifluorenyl group and the spirobenzoanthracenefluorenyl group are substituted,

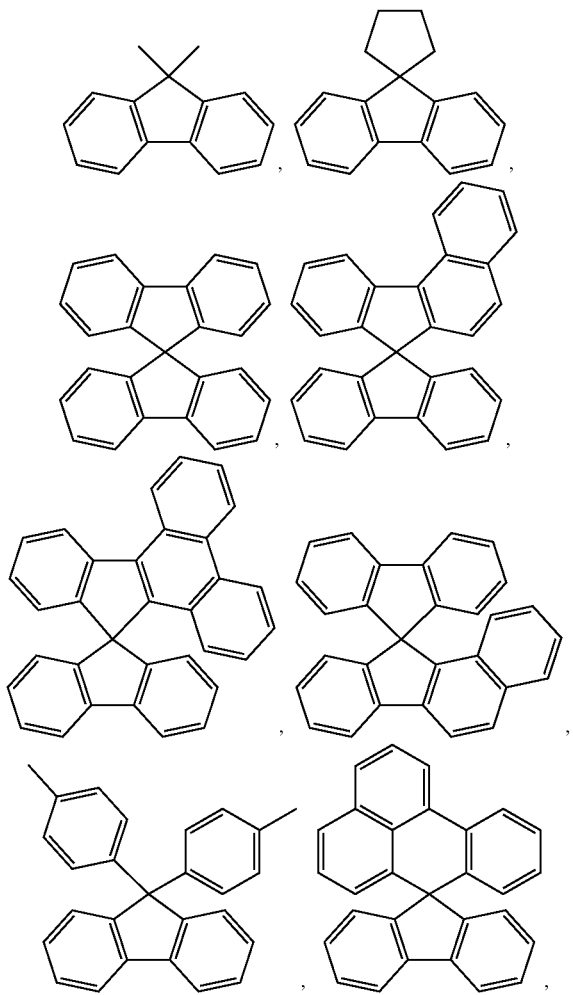

-continued

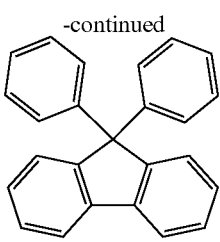

and the like may be included. However, the structure is not limited thereto.

In the present specification, descriptions on the aryl group provided above may be applied to the aryl group in the arylamine group, the aryloxy group, the aralkyl group and the alkylaryl group.

In the present specification, examples of the aryloxy group may include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, descriptions on the aryl group provided above may be applied to the arylene group except for being a divalent.

In the present specification, descriptions on the heteroaryl group provided above may be applied to the heteroarylene group except for being a divalent.

According to one embodiment of the present specification, the electron transfer layer comprises a compound having a structure of an electron donor and an electron acceptor bonding to each other.

According to one embodiment of the present specification, at least one of $R_1$ to $R_5$ is each independently represented by -$(L_1)z_1$-$A_1$, and the rest of $R_1$ to $R_5$ that are not -$(L_1)z_1$-$A_1$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group.

According to one embodiment of the present specification, the rest of $R_1$ to $R_5$ that are not -$(L_1)z_1$-$A_1$ are hydrogen.

According to one embodiment of the present specification, at least one of $Ar_1$ to $Ar_3$ is each independently represented by -$(L_2)z_2$-$A_2$, and the rest of $Ar_1$ to $Ar_3$ that are not -$(L_2)z_2$-$A_2$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group.

According to one embodiment of the present specification, the rest of $Ar_1$ to $Ar_3$ that are not -($L_2$)$z_2$-$A_2$ are hydrogen.

According to one embodiment of the present specification, $a_1+a_2+a_3=3$.

According to one embodiment of the present specification, $a_1=1$, $a_2=1$ and $a_3=1$.

According to one embodiment of the present specification, $L_1$ and $L_2$ are the same as or different from each other, and each independently a direct bond; an arylene group unsubstituted or substituted with an alkyl group, a cycloalkyl group or an aryl group; or a heteroarylene group unsubstituted or substituted with an alkyl group, a cycloalkyl group or an aryl group.

According to one embodiment of the present specification, $L_1$ and $L_2$ are the same as or different from each other, and each independently a direct bond; an arylene group having 6 to 50 carbon atoms unsubstituted or substituted with an alkyl group having 1 to 50 carbon atoms, a cycloalkyl group having 3 to 50 carbon atoms or an aryl group having 6 to 50 carbon atoms; or a heteroarylene group having 2 to 50 carbon atoms unsubstituted or substituted with an alkyl group having 1 to 50 carbon atoms, a cycloalkyl group having 3 to 50 carbon atoms or an aryl group having 6 to 50 carbon atoms.

According to one embodiment of the present specification, $L_1$ and $L_2$ are the same as or different from each other, and each independently a direct bond; a phenylene group; a naphthylene group; a biphenylylene group; a terphenylylene group; a fluorenylene group unsubstituted or substituted with an alkyl group or an aryl group; a phenanthrylene group; an anthracenylene group; a divalent thiophene group; a furanylene group; a pyrrolene group unsubstituted or substituted with an alkyl group or an aryl group; a dibenzofuranylene group; a divalent dibenzothiophene group; or a carbazolylene group unsubstituted or substituted with an alkyl group or an aryl group.

According to one embodiment of the present specification, $L_1$ and $L_2$ are the same as or different from each other, and each independently a direct bond; a phenylene group; a naphthylene group; a biphenylylene group; a terphenylylene group; a fluorenylene group unsubstituted or substituted with an alkyl group having 1 to 50 carbon atoms or an aryl group having 6 to 50 carbon atoms; a phenanthrylene group; an anthracenylene group; a divalent thiophene group; a furanylene group; a pyrrolene group unsubstituted or substituted with an alkyl group having 1 to 50 carbon atoms or an aryl group having 6 to carbon atoms; a dibenzofuranylene group; a divalent dibenzothiophene group; or a carbazolylene group unsubstituted or substituted with an alkyl group having 1 to 50 carbon atoms or an aryl group having 6 to 50 carbon atoms.

According to one embodiment of the present specification, $L_1$ is a substituted or unsubstituted arylene group.

According to one embodiment of the present specification, $L_1$ is a substituted or unsubstituted arylene group having 6 to 50 carbon atoms.

According to one embodiment of the present specification, $L_1$ is an arylene group.

According to one embodiment of the present specification, $L_1$ is an arylene group having 6 to 50 carbon atoms.

According to one embodiment of the present specification, $L_1$ is a substituted or unsubstituted phenylene group.

According to one embodiment of the present specification, $L_1$ is a phenylene group.

According to one embodiment of the present specification, $L_2$ is a direct bond.

According to one embodiment of the present specification, $A_1$ is a substituted or unsubstituted heteroaryl group comprising one or more Ns.

According to one embodiment of the present specification, $A_1$ is a substituted or unsubstituted heteroaryl group having 2 to 50 carbon atoms comprising one or more Ns.

According to one embodiment of the present specification, $A_1$ is a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted oxazole group; a substituted or unsubstituted isoxazole group; a substituted or unsubstituted triazole group; a substituted or unsubstituted triazole group; a substituted or unsubstituted isothiazole group; a substituted or unsubstituted oxadiazole group; a substituted or unsubstituted thiadiazole group; a substituted or unsubstituted dithiazole group; a substituted or unsubstituted tetrazole group; a substituted or unsubstituted diazine group; a substituted or unsubstituted oxazine group; a substituted or unsubstituted triazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzothiazole group; a substituted or unsubstituted benzoxazole group; a substituted or unsubstituted benzimidazole group; a substituted or unsubstituted carbazole group; a substituted or unsubstituted benzocarbazole group; a substituted or unsubstituted phenazine group; or a substituted or unsubstituted phenoxazine group.

According to one embodiment of the present specification, $A_1$ is a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted triazole group; a substituted or unsubstituted triazine group; a substituted or unsubstituted carbazole group; a substituted or unsubstituted tetrazole group; a substituted or unsubstituted diazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzimidazole group; a substituted or unsubstituted benzocarbazole group; or a substituted or unsubstituted phenazine group.

According to one embodiment of the present specification, $A_1$ is a pyridine group unsubstituted or substituted with an aryl group or a heteroaryl group; a pyrrole group unsubstituted or substituted with an aryl group or a heteroaryl group; a pyrimidine group unsubstituted or substituted with an aryl group or a heteroaryl group; a pyridazine group unsubstituted or substituted with an aryl group or a heteroaryl group; an imidazole group unsubstituted or substituted with an aryl group or a heteroaryl group; a pyrazole group unsubstituted or substituted with an aryl group or a heteroaryl group; a triazole group unsubstituted or substituted with an aryl group or a heteroaryl group; a triazine group unsubstituted or substituted with an aryl group or a heteroaryl group; a carbazole group unsubstituted or substituted with an aryl group or a heteroaryl group; a tetrazole group unsubstituted or substituted with an aryl group or a heteroaryl group; a diazine group unsubstituted or substituted with an aryl group or a heteroaryl group; an isoquinoline group unsubstituted or substituted with an aryl group or a heteroaryl group; a quinoline group unsubstituted or substituted with an aryl group or a heteroaryl group; a quinol group unsubstituted or substituted with an aryl group or a heteroaryl group; a quinazoline group unsubstituted or substituted with an aryl group or a heteroaryl group; a quinoxaline group unsubstituted or substituted with an aryl group or a heteroaryl group; an acridine group unsubstituted or substituted with an aryl group or a heteroaryl group; a phenanthridine group unsubstituted or substituted with an aryl group or a heteroaryl group; a diazanaphthalene group unsubstituted or substituted with an aryl group or a heteroaryl group; an indole group unsubstituted or substituted with an aryl group or a heteroaryl group; a benzimidazole group unsubstituted or substituted with an aryl group or a heteroaryl group; a benzocarbazole group unsubstituted or substituted with an aryl group or a heteroaryl group; or a phenazine group unsubstituted or substituted with an aryl group or a heteroaryl group.

According to one embodiment of the present specification, $A_1$ is a triazine group unsubstituted or substituted with an aryl group or a heteroaryl group; or a carbazole group unsubstituted or substituted with an aryl group or a heteroaryl group.

According to one embodiment of the present specification, $A_1$ is a triazine group unsubstituted or substituted with an aryl group; or a carbazole group unsubstituted or substituted with an aryl group.

According to one embodiment of the present specification, $A_1$ is a triazine group unsubstituted or substituted with an aryl group.

According to one embodiment of the present specification, $A_1$ a triazine group unsubstituted or substituted with a phenyl group.

According to one embodiment of the present specification, $R_5$ may be represented by -$(L_1)z_1$-$A_1$.

According to one embodiment of the present specification, $R_1$ to $R_4$ are hydrogen.

According to one embodiment of the present specification, $R_5$ is represented by -$(L_1)z_1$-$A_1$, and $R_1$ to $R_4$ are hydrogen.

According to one embodiment of the present specification, Chemical Formula 1 may be represented by the following Chemical Formula 4.

[Chemical Formula 4]

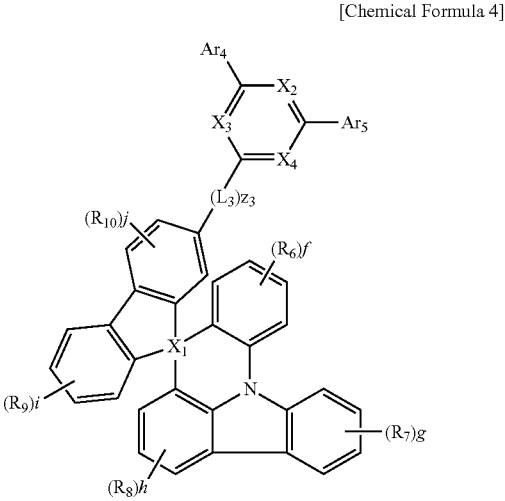

In Chemical Formula 4, $X_2$ to $X_4$ are the same as or different from each other, and each independently CR; or N, and at least one of $X_2$ to $X_4$ is N, $Ar_4$ and $Ar_5$ are the same as or different from each other, and each independently a substituted or unsubstituted aryl group; or a substituted or unsubstituted heteroaryl group, $L_3$ is a direct bond; or a divalent group comprising one or more types selected from the group consisting of a substituted or unsubstituted arylene group and a substituted or unsubstituted heteroarylene group, $z_3$ is an integer of 1 or 2, and when $z_3$ is 2, $L_3$s are the same as or different from each other, R and $R_6$ to $R_{10}$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, f, g and i are the same as or different from each other and each independently an integer of 1 to 4, h and j are the same as or different from each other and each independently an integer of 1 to 3, and when f to j are each 2 or greater, substituents in the parentheses are the same as or different from each other, and the rest of the substituents have the same definitions as in Chemical Formula 1.

According to one embodiment of the present specification, $L_3$ is a direct bond; an arylene group unsubstituted or substituted with an alkyl group, a cycloalkyl group or an aryl group; or a heteroarylene group unsubstituted or substituted with an alkyl group, a cycloalkyl group or an aryl group.

According to one embodiment of the present specification, $L_3$s are the same as or different from each other, and each independently a direct bond; an arylene group having 6 to 50 carbon atoms unsubstituted or substituted with an alkyl group having 1 to 50 carbon atoms, a cycloalkyl group having 3 to 50 carbon atoms or an aryl group having 6 to 50 carbon atoms; or a heteroarylene group having 2 to 50 carbon atoms unsubstituted or substituted with an alkyl group having 1 to 50 carbon atoms, a cycloalkyl group having 3 to 50 carbon atoms or an aryl group having 6 to 50 carbon atoms.

According to one embodiment of the present specification, $L_3$s are the same as or different from each other, and each independently a direct bond; a phenylene group; a naphthylene group; a biphenylylene group; a terphenylylene group; a fluorenylene group unsubstituted or substituted with an alkyl group or an aryl group; a phenanthrylene group; an anthracenylene group; a divalent thiophene group; a furanylene group; a pyrrolene group unsubstituted or substituted with an alkyl group or an aryl group; a dibenzofuranylene group; a divalent dibenzothiophene group; or a carbazolylene group unsubstituted or substituted with an alkyl group or an aryl group.

According to one embodiment of the present specification, $L_3$s are the same as or different from each other, and each independently a direct bond; a phenylene group; a naphthylene group; a biphenylylene group; a terphenylylene group; a fluorenylene group unsubstituted or substituted with an alkyl group having 1 to 50 carbon atoms or an aryl group having 6 to carbon atoms; a phenanthrylene group; an anthracenylene group; a divalent thiophene group; a furanylene group; a pyrrolene group unsubstituted or substituted with an alkyl group having 1 to 50 carbon atoms or an aryl group having 6 to carbon atoms; a dibenzofuranylene group; a divalent dibenzothiophene group; or a carbazolylene group unsubstituted or substituted with an alkyl group having 1 to 50 carbon atoms or an aryl group having 6 to 50 carbon atoms.

According to one embodiment of the present specification, $L_3$ is a substituted or unsubstituted arylene group.

According to one embodiment of the present specification, $L_3$ is a substituted or unsubstituted arylene group having 6 to 50 carbon atoms.

According to one embodiment of the present specification, $L_3$ is an arylene group.

According to one embodiment of the present specification, $L_3$ is an arylene group having 6 to 50 carbon atoms.

According to one embodiment of the present specification, $L_3$ is a substituted or unsubstituted phenylene group.

According to one embodiment of the present specification, $L_3$ is a phenylene group.

According to one embodiment of the present specification, $X_1$ is C.

According to one embodiment of the present specification, $X_1$ is Si.

According to one embodiment of the present specification, $X_2$ to $X_4$ are N.

According to one embodiment of the present specification, $R_6$ to $R_{10}$ are hydrogen.

According to one embodiment of the present specification, $Ar_4$ and $Ar_5$ are the same as or different from each other, and each independently a substituted or unsubstituted aryl group having 6 to 50 carbon atoms; or a substituted or unsubstituted heteroaryl group having 2 to 50 carbon atoms.

According to one embodiment of the present specification, $Ar_4$ and $Ar_5$ are the same as or different from each other, and each independently an aryl group having 6 to 50 carbon atoms unsubstituted or substituted with a halogen group, a cyano group, an alkoxy group, an alkyl group, a silyl group, an aryl group or a heteroaryl group; or a heteroaryl group having 2 to 50 carbon atoms unsubstituted or substituted with a halogen group, a cyano group, an alkyl group, a cycloalkyl group, a silyl group, an aryl group or a heteroaryl group.

According to one embodiment of the present specification, $Ar_4$ and $Ar_5$ are the same as or different from each other, and each independently an aryl group having 6 to 50 carbon atoms unsubstituted or substituted with a halogen group, a cyano group, an alkoxy group having 1 to 50 carbon atoms, an alkyl group having 1 to 50 carbon atoms, a silyl group, an aryl group having 6 to 50 carbon atoms or a heteroaryl group having 2 to 50 carbon atoms; or a heteroaryl group having 2 to 50 carbon atoms unsubstituted or substituted with a halogen group, a cyano group, an alkyl group having 1 to 50 carbon atoms, a cycloalkyl group having 3 to 50 carbon atoms, a silyl group, an aryl group having 6 to 50 carbon atoms or a heteroaryl group having 2 to 50 carbon atoms.

According to one embodiment of the present specification, $Ar_4$ and $Ar_5$ are the same as or different from each other, and each independently an aryl group having 6 to 50 carbon atoms unsubstituted or substituted with an alkyl group, a cycloalkyl group, an aryl group, an alkoxy group, a halogen group, a cyano group, a silyl group, a heteroaryl group or a substituent formed with two or more combinations thereof; or a heteroaryl group having 2 to 50 carbon atoms unsubstituted or substituted with an alkyl group, a cycloalkyl group, an aryl group, an alkoxy group, a halogen group, a cyano group, a silyl group, a heteroaryl group or a substituent formed with two or more combinations thereof.

According to one embodiment of the present specification, $Ar_4$ and $Ar_5$ are the same as or different from each other, and each independently a phenyl group unsubstituted or substituted with an alkyl group, an aryl group, an alkoxy group, a halogen group, a cyano group, a silyl group, a heteroaryl group or a substituent formed with two or more combinations thereof; a biphenyl group unsubstituted or substituted with an alkyl group, a halogen group, a cyano group or an alkylsilyl group; a terphenyl group unsubstituted or substituted with an alkyl group, a halogen group, a cyano group or an alkylsilyl group; a naphthyl group unsubstituted or substituted with an alkyl group, a halogen group, a cyano group or an alkylsilyl group; a fluorenyl group unsubstituted or substituted with an alkyl group, a halogen group, a cyano group, an alkylsilyl group or an aryl group; a benzofluorenyl group unsubstituted or substituted with an alkyl group; a phenanthrenyl group; an anthracenyl group; a dibenzofuranyl group unsubstituted or substituted with an alkyl group or a cycloalkyl group; a naphthobenzofuranyl group; a dibenzothiophene group unsubstituted or substituted with an alkyl group or a cycloalkyl group; a carbazolyl group unsubstituted or substituted with an alkyl group or an aryl group; a thiophene group unsubstituted or substituted with an alkyl group, an aryl group, a heteroaryl group or a substituent formed with two or more combinations thereof; a quinolyl group; an isoquinolyl group; a pyridazinyl group; a triazinyl group; a pyrimidinyl group; a pyridinyl group; a benzoxazolyl group; a benzothiazolyl group; a benzoxathiolyl group; a pyrenyl group; a fluoranthenyl group; a spirobifluorenyl group; a benzimidazolyl group unsubstituted or substituted with an alkyl group or an aryl group; a quinoxalinyl group; or a triphenylenyl group.

According to one embodiment of the present specification, $Ar_4$ and $Ar_5$ are the same as or different from each other, and each independently a phenyl group unsubstituted or substituted with an alkyl group having 1 to 50 carbon atoms, an aryl group having 6 to 50 carbon atoms, an alkoxy group having 1 to 50 carbon atoms, a halogen group, a cyano group, an alkylsilyl group having 1 to 50 carbon atoms, a heteroaryl group having 2 to 50 carbon atoms or a substituent formed with two or more combinations thereof; a biphenyl group unsubstituted or substituted with an alkyl group having 1 to 50 carbon atoms, a halogen group, a cyano group or an alkylsilyl group having 1 to 50 carbon atoms; a terphenyl group unsubstituted or substituted with an alkyl group having 1 to 50 carbon atoms, a halogen group, a cyano group or an alkylsilyl group having 1 to 50 carbon atoms; a naphthyl group unsubstituted or substituted with an alkyl group having 1 to 50 carbon atoms, a halogen group, a cyano group or an alkylsilyl group having 1 to 50 carbon atoms; a fluorenyl group unsubstituted or substituted with an alkyl group having 1 to 50 carbon atoms, a halogen group, a cyano group, an alkylsilyl group having 1 to 50 carbon atoms or an aryl group having 6 to 50 carbon atoms; a benzofluorenyl group unsubstituted or substituted with an alkyl group having 1 to 50 carbon atoms; a phenanthrenyl group; an anthracenyl group; a dibenzofuranyl group unsubstituted or substituted with an alkyl group having 1 to 50 carbon atoms or a cycloalkyl group having 3 to 50 carbon atoms; a naphthobenzofuranyl group; a dibenzothiophene group unsubstituted or substituted with an alkyl group having 1 to 50 carbon atoms or a cycloalkyl group having 3 to 50 carbon atoms; a carbazolyl group unsubstituted or substituted with an alkyl group having 1 to 50 carbon atoms or an aryl group having 6 to 50 carbon atoms; a thiophene group unsubstituted or substituted with an alkyl group having 1 to 50 carbon atoms, an aryl group having 6 to 50 carbon atoms, a heteroaryl group having 2 to 50 carbon atoms or a substituent formed with two or more combinations thereof; a quinolyl group; an isoquinolyl group; a pyridazinyl group; a triazinyl group; a pyrimidinyl group; a pyridinyl group; a benzoxazolyl group; a benzothiazolyl group; a benzoxathiolyl group; a pyrenyl group; a fluoranthenyl group; a spirobifluorenyl group; a benzimidazolyl group unsubstituted or substituted with an alkyl group having 1 to 50 carbon atoms or an aryl group having 6 to 50 carbon atoms; a quinoxalinyl group; or a triphenylenyl group.

According to one embodiment of the present specification, $Ar_4$ and $Ar_5$ are the same as each other.

According to one embodiment of the present specification, $Ar_4$ and $Ar_5$ are different from each other.

According to one embodiment of the present specification, $Ar_4$ and $Ar_5$ are the same as or different from each other, and each independently a substituted or unsubstituted aryl group having 6 to 50 carbon atoms.

According to one embodiment of the present specification, $Ar_4$ and $Ar_5$ are the same as or different from each other, and each independently an aryl group having 6 to 50 carbon atoms.

According to one embodiment of the present specification, $Ar_4$ and $Ar_5$ are the same as or different from each other, and each independently a phenyl group; or a biphenyl group.

According to one embodiment of the present specification, $Ar_4$ and $Ar_5$ are a phenyl group.

According to one embodiment of the present specification, $A_2$ is a substituted or unsubstituted aryl group; or a substituted or unsubstituted heteroaryl group comprising one or more Ns.

According to one embodiment of the present specification, $A_2$ is a substituted or unsubstituted aryl group; or a substituted or unsubstituted heteroaryl group having 2 to 50 carbon atoms comrising one or more Ns.

According to one embodiment of the present specification, $A_2$ is a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted perylenyl group; a substituted or unsubstituted fluoranthenyl group; a substituted or unsubstituted triphenylenyl group; a substituted or unsubstituted phenalenyl group; a substituted or unsubstituted chrysenyl group; a substituted or unsubstituted fluorenyl group; a substituted or unsubstituted benzofluorenyl group; a substituted or unsubstituted spirobifluorenyl group; a substituted or unsubstituted triphenylene group; a substituted or unsubstituted spirobenzoanthracenefluorenyl group; a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted oxazole group; a substituted or unsubstituted isoxazole group; a substituted or unsubstituted triazole group; a substituted or unsubstituted triazole group; a substituted or unsubstituted isothiazole group; a substituted or unsubstituted oxadiazole group; a substituted or unsubstituted thiadiazole group; a substituted or unsubstituted dithiazole group; a substituted or unsubstituted tetrazole group; a substituted or unsubstituted diazine group; a substituted or unsubstituted oxazine group; a substituted or unsubstituted triazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzothiazole group; a substituted or unsubstituted benzoxazole group; a substituted or unsubstituted benzimidazole group; a substituted or unsubstituted carbazole group; a substituted or unsubstituted benzocarbazole group; a substituted or unsubstituted phenazine group; or a substituted or unsubstituted phenoxazine group.

According to one embodiment of the present specification, $A_2$ is a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted perylenyl group; a substituted or unsubstituted fluoranthenyl group; a substituted or unsubstituted triphenylenyl group; a substituted or unsubstituted phenalenyl group; a substituted or unsubstituted chrysenyl group; a substituted or unsubstituted fluorenyl group; a substituted or unsubstituted benzofluorenyl group; a substituted or unsubstituted spirobifluorenyl group; a substituted or unsubstituted triphenylene group; a substituted or unsubstituted spirobenzoanthracenefluorenyl group; a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted triazole group; a substituted or unsubstituted triazine group; a substituted or unsubstituted carbazole group; a substituted or unsubstituted tetrazole group; a substituted or unsubstituted diazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzimidazole group; a substituted or unsubstituted benzocarbazole group; or a substituted or unsubstituted phenazine group.

According to one embodiment of the present specification, $A_2$ is a phenyl group unsubstituted or substituted with an aryl group or a heteroaryl group; a biphenyl group unsubstituted or substituted with an aryl group or a heteroaryl group; a terphenyl group unsubstituted or substituted with an aryl group or a heteroaryl group; a naphthyl group unsubstituted or substituted with an aryl group or a heteroaryl group; an anthracenyl group unsubstituted or substituted with an aryl group or a heteroaryl group; a phenanthrenyl group unsubstituted or substituted with an aryl group or a heteroaryl group; a pyrenyl group unsubstituted or substituted with an aryl group or a heteroaryl group; a perylenyl group unsubstituted or substituted with an aryl group or a heteroaryl group; a fluoranthenyl group unsubstituted or substituted with an aryl group or a heteroaryl group; a triphenylenyl group unsubstituted or substituted with an aryl group or a heteroaryl group; a phenalenyl group unsubstituted or substituted with an aryl group or a heteroaryl group; a chrysenyl group unsubstituted or substituted with an aryl group or a heteroaryl group; a fluorenyl group unsubstituted or substituted with an aryl group or a heteroaryl group; a benzofluorenyl group unsubstituted or substituted with an aryl group or a heteroaryl group; a spirobifluorenyl group unsubstituted or substituted with an aryl group or a heteroaryl group; a triphenylene group unsubstituted or substituted with an aryl group or a heteroaryl group; a spirobenzoanthracenefluorenyl group unsubstituted or substituted with an aryl group or a heteroaryl group; a pyridine group unsubstituted or substituted with an aryl group or a heteroaryl group; a pyrrole group unsubstituted or substituted with an aryl group or a heteroaryl group; a pyrimidine group unsubstituted or substituted with an aryl group or a heteroaryl group; a pyridazine group unsubstituted or substituted with an aryl group or a heteroaryl group; an imidazole group unsubstituted or substituted with an aryl group or a heteroaryl group; a pyrazole group unsubstituted or substituted with an aryl group or a heteroaryl group; a triazole group unsubstituted or substituted with an aryl group or a heteroaryl group; a triazine group unsubstituted or substituted with an aryl group or a heteroaryl group; a carbazole group unsubstituted or substituted with an aryl group or a heteroaryl group; a tetrazole group unsubstituted or substituted with an aryl group or a heteroaryl group; a diazine group unsubstituted or substituted with an aryl group or a heteroaryl group; an isoquinoline group unsubstituted or substituted with an aryl group or a heteroaryl group; a quinoline group unsubstituted or substituted with an aryl group or a heteroaryl group; a quinol group unsubstituted or substituted with an aryl group or a heteroaryl group; a quinazoline group unsubstituted or substituted with an aryl group or a heteroaryl group; a quinoxaline group unsubstituted or substituted with an aryl group or a heteroaryl group; an acridine group unsubstituted or substituted with an aryl group or a heteroaryl group; a phenanthridine group unsubstituted or substituted with an aryl group or a heteroaryl group; a diazanaphthalene group unsubstituted or substituted with an aryl group or a heteroaryl group; an indole group unsubstituted or substituted with an aryl group or a heteroaryl group; a benzimidazole group unsubstituted or substituted with an aryl group or a heteroaryl group; a benzocarbazole group unsubstituted or substituted with an aryl group or a heteroaryl group; or a phenazine group unsubstituted or substituted with an aryl group or a heteroaryl group.

According to one embodiment of the present specification, $A_2$ is a phenyl group unsubstituted or substituted with an aryl group or a heteroaryl group; a biphenyl group unsubstituted or substituted with an aryl group or a heteroaryl group; a naphthyl group unsubstituted or substituted with an aryl group or a heteroaryl group; an anthracenyl group unsubstituted or substituted with an aryl group or a heteroaryl group; a phenanthrenyl group unsubstituted or substituted with an aryl group or a heteroaryl group; a pyrenyl group unsubstituted or substituted with an aryl group or a heteroaryl group; a perylenyl group unsubstituted or substituted with an aryl group or a heteroaryl group; a fluoranthenyl group unsubstituted or substituted with an aryl group or a heteroaryl group; a chrysenyl group unsubstituted or substituted with an aryl group or a heteroaryl group; a fluorenyl group unsubstituted or substituted with an aryl group or a heteroaryl group; a benzofluorenyl group unsubstituted or substituted with an aryl group or a heteroaryl group; a pyrimidine group unsubstituted or substituted with an aryl group or a heteroaryl group; a triazine group unsubstituted or substituted with an aryl group or a heteroaryl group; or a carbazole group unsubstituted or substituted with an aryl group or a heteroaryl group.

According to one embodiment of the present specification, $A_2$ is a phenyl group unsubstituted or substituted with an aryl group; a biphenyl group unsubstituted or substituted with an aryl group; a naphthyl group unsubstituted or substituted with an aryl group; an anthracenyl group unsubstituted or substituted with an aryl group; a phenanthrenyl group unsubstituted or substituted with an aryl group; a pyrenyl group unsubstituted or substituted with an aryl group; a perylenyl group unsubstituted or substituted with an aryl group; a pyrimidine group unsubstituted or substituted with an aryl group; a triazine group unsubstituted or substituted with an aryl group; or a carbazole group unsubstituted or substituted with an aryl group.

According to one embodiment of the present specification, $A_2$ is a substituted or unsubstituted phenanthrenyl group; a substituted or unsubstituted pyrimidine group; a substituted or unsubstituted triazine group; or a substituted or unsubstituted carbazole group.

According to one embodiment of the present specification, $A_2$ is a phenyl group unsubstituted or substituted with a phenyl group, a biphenyl group, a terphenyl group or a naphthyl group; a phenanthrenyl group unsubstituted or substituted with a phenyl group, a biphenyl group, a terphenyl group or a naphthyl group; a pyrimidine group unsubstituted or substituted with a phenyl group, a biphenyl group, a terphenyl group or a naphthyl group; a triazine group unsubstituted or substituted with a phenyl group, a biphenyl group, a terphenyl group or a naphthyl group; or a carbazole group unsubstituted or substituted with a phenyl group, a biphenyl group, a terphenyl group or a naphthyl group.

According to one embodiment of the present specification, Chemical Formula 2 may be represented by the following Chemical Formula 5 or Chemical Formula 6.

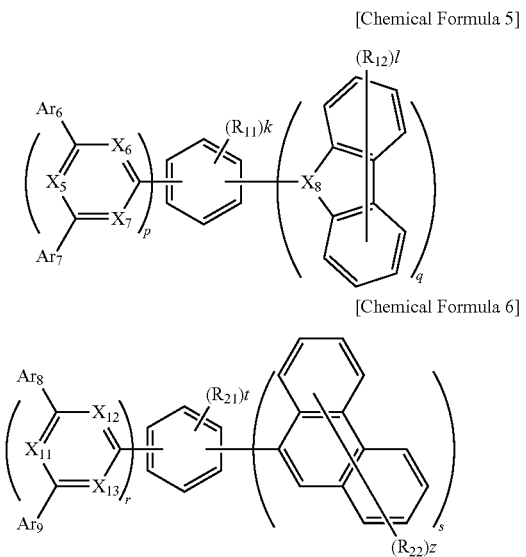

[Chemical Formula 5]

[Chemical Formula 6]

In Chemical Formulae 5 and 6, $X_5$ to $X_8$ and $X_{11}$ to $X_{13}$ are the same as or different from each other, and each independently CR'; or N, and at least one of $X_5$ to $X_7$ is N and at least one of $X_{11}$ to $X_{13}$ is N, $Ar_6$ to $Ar_9$ are the same as or different from each other, and each independently a substituted or unsubstituted aryl group; or a substituted or unsubstituted heteroaryl group, R' and $R_{11}$, $R_{12}$, $R_{21}$ and $R_{22}$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, k and t are the same as or different from each other and each independently an integer of 1 to 4, 1 is an integer of 1 to 8, z is an integer of 1 to 9, p and r are the same as or different from each other and each independently an integer of 1 or greater, q and s are the same as or different from each other and each independently an integer of 1 or greater, p+q+k≤6, t+r+s≤6, and when k, l, p, q, r, s, t and z are each 2 or greater, substituents in the parentheses are the same as or different from each other.

According to one embodiment of the present specification, at least two or more of $X_5$ to $X_7$ are N.

According to one embodiment of the present specification, at least two or more of $X_{11}$ to $X_{13}$ are N.

According to one embodiment of the present specification, $X_5$ and $X_{11}$ are N, at least one of $X_6$ and $X_7$ is N, and at least one of $X_{12}$ and $X_{13}$ is N.

According to one embodiment of the present specification, R' is hydrogen.

According to one embodiment of the present specification, $R_{11}$ and $R_{12}$ are hydrogen.

According to one embodiment of the present specification, $R_{21}$ and $R_{22}$ are hydrogen.

According to one embodiment of the present specification, p+q≤3.

According to one embodiment of the present specification, r+s≤3.

According to one embodiment of the present specification, p is 1.

According to one embodiment of the present specification, q is 2.

According to one embodiment of the present specification, r is 1.

According to one embodiment of the present specification, s is 2.

According to one embodiment of the present specification, $X_8$ is N.

According to one embodiment of the present specification, Chemical Formula 2 may be represented by the following Chemical Formula 2-1.

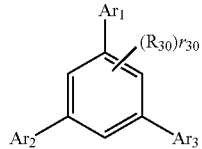

[Chemical Formula 2-1]

In Chemical Formula 2-1, $R_{30}$ is selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, $r_{30}$ is an integer of 1 to 3, and when $r_{30}$ is 2 or greater, $R_{10}$s are the same as or different from each other, and the rest of the substituents have the same definitions as in Chemical Formula 2.

According to one embodiment of the present specification, $R_{30}$ is hydrogen.

According to one embodiment of the present specification, Chemical Formula 5 may be represented by the following Chemical Formula 5-1.

[Chemical Formula 5-1]

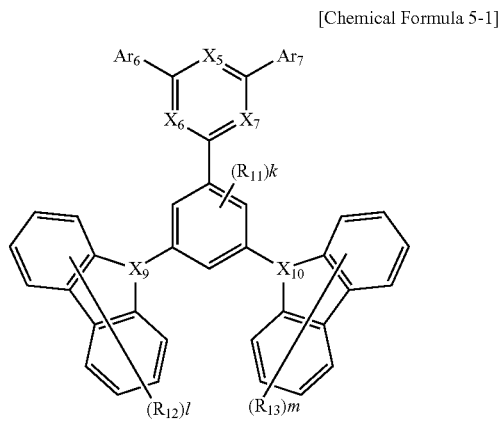

In Chemical Formula 5-1, $R_{13}$ has the same definition as $R_{11}$ and $R_{12}$ in Chemical Formula 5, $X_9$ and $X_{10}$ have the same definitions as $X_8$ in Chemical Formula 5, k is an integer of 1 to 3, m is an integer of 1 to 8, and when k and m are each an integer of 2 or greater, substituents in the parentheses are the same as or different from each other, and the rest of the substituents have the same definitions as in Chemical Formula 5.

According to one embodiment of the present specification, $X_9$ and $X_{10}$ are N.

According to one embodiment of the present specification, $R_{13}$ is hydrogen.

According to one embodiment of the present specification, Chemical Formula 6 may be represented by the following Chemical Formula 6-1.

[Chemical Formula 6-1]

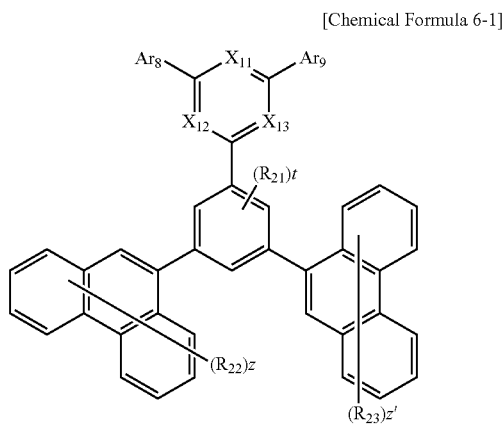

In Chemical Formula 6-1, $R_{23}$ has the same definition as $R_{21}$ and $R_{22}$ in Chemical Formula 6, t is an integer of 1 to 3, z' is an integer of 1 to 9, and when t and z' are each an integer of 2 or greater, substituents in the parentheses are the same as or different from each other, and the rest of the substituents have the same definitions as in Chemical Formula 6.

According to one embodiment of the present specification, $X_{11}$ to $X_{13}$ are N.

According to one embodiment of the present specification, $R_{23}$ is hydrogen.

According to one embodiment of the present specification, $Ar_6$ and $Ar_7$ are the same as or different from each other, and each independently a substituted or unsubstituted aryl group having 6 to 50 carbon atoms; or a substituted or unsubstituted heteroaryl group having 2 to 50 carbon atoms.

According to one embodiment of the present specification, $Ar_6$ and $Ar_7$ are the same as or different from each other, and each independently an aryl group having 6 to 50 carbon atoms unsubstituted or substituted with a halogen group, a cyano group, an alkoxy group, an alkyl group, a silyl group, an aryl group or a heteroaryl group; or a heteroaryl group having 2 to 50 carbon atoms unsubstituted or substituted with a halogen group, a cyano group, an alkyl group, a cycloalkyl group, a silyl group, an aryl group or a heteroaryl group.

According to one embodiment of the present specification, $Ar_6$ and $Ar_7$ are the same as or different from each other, and each independently an aryl group having 6 to 50 carbon atoms unsubstituted or substituted with a halogen group, a cyano group, an alkoxy group having 1 to 50 carbon atoms, an alkyl group having 1 to 50 carbon atoms, a silyl group, an aryl group having 6 to 50 carbon atoms or a heteroaryl group having 2 to 50 carbon atoms; or a heteroaryl group having 2 to 50 carbon atoms unsubstituted or substituted with a halogen group, a cyano group, an alkyl group having 1 to 50 carbon atoms, a cycloalkyl group having 3 to 50 carbon atoms, a silyl group, an aryl group having 6 to 50 carbon atoms or a heteroaryl group having 2 to 50 carbon atoms.

According to one embodiment of the present specification, $Ar_6$ and $Ar_7$ are the same as or different from each other, and each independently an aryl group having 6 to 50 carbon atoms unsubstituted or substituted with an alkyl group, a cycloalkyl group, an aryl group, an alkoxy group, a halogen group, a cyano group, a silyl group, a heteroaryl group or a substituent formed with two or more combinations thereof; or a heteroaryl group having 2 to 50 carbon atoms unsubstituted or substituted with an alkyl group, a cycloalkyl group, an aryl group, an alkoxy group, a halogen group, a cyano group, a silyl group, a heteroaryl group or a substituent formed with two or more combinations thereof.

According to one embodiment of the present specification, $Ar_6$ and $Ar_7$ are the same as or different from each other, and each independently a phenyl group unsubstituted or substituted with an alkyl group, an aryl group, an alkoxy group, a halogen group, a cyano group, a silyl group, a heteroaryl group or a substituent formed with two or more combinations thereof; a biphenyl group unsubstituted or substituted with an alkyl group, a halogen group, a cyano group or an alkylsilyl group; a terphenyl group unsubstituted or substituted with an alkyl group, a halogen group, a cyano group or an alkylsilyl group; a naphthyl group unsubstituted or substituted with an alkyl group, a halogen group, a cyano group or an alkylsilyl group; a fluorenyl group unsubstituted or substituted with an alkyl group, a halogen group, a cyano group, an alkylsilyl group or an aryl group; a benzofluorenyl group unsubstituted or substituted with an alkyl group; a phenanthrenyl group; an anthracenyl group; a dibenzofuranyl group unsubstituted or substituted with an alkyl group or a cycloalkyl group; a naphthobenzofuranyl group; a dibenzothiophene group unsubstituted or substituted with an alkyl group or a cycloalkyl group; a carbazolyl group unsubstituted or substituted with an alkyl group or an aryl group; a thiophene group unsubstituted or substituted with an alkyl group, an aryl group, a heteroaryl group or a substituent formed with two or more combinations thereof; a quinolyl group; an isoquinolyl group; a pyridazinyl group; a triazinyl group; a pyrimidinyl group; a pyridinyl group; a benzoxazolyl group; a benzothiazolyl group; a benzoxathiolyl group; a pyrenyl group; a fluoranthenyl group; a spirobifluorenyl group; a benzimidazolyl group unsubstituted or substituted with an alkyl group or an aryl group; a quinoxalinyl group; or a triphenylenyl group.

According to one embodiment of the present specification, $Ar_6$ and $Ar_7$ are the same as or different from each other, and each independently a phenyl group unsubstituted or substituted with an alkyl group having 1 to 50 carbon atoms, an aryl group having 6 to 50 carbon atoms, an alkoxy group having 1 to 50 carbon atoms, a halogen group, a cyano group, an alkylsilyl group having 1 to 50 carbon atoms, a heteroaryl group having 2 to 50 carbon atoms or a substituent formed with two or more combinations thereof; a biphenyl group unsubstituted or substituted with an alkyl group having 1 to 50 carbon atoms, a halogen group, a cyano group or an alkylsilyl group having 1 to 50 carbon atoms; a terphenyl group unsubstituted or substituted with an alkyl group having 1 to 50 carbon atoms, a halogen group, a cyano group or an alkylsilyl group having 1 to 50 carbon atoms; a naphthyl group unsubstituted or substituted with an alkyl group having 1 to 50 carbon atoms, a halogen group, a cyano group or an alkylsilyl group having 1 to 50 carbon atoms; a fluorenyl group unsubstituted or substituted with an alkyl group having 1 to 50 carbon atoms, a halogen group, a cyano group, an alkylsilyl group having 1 to 50 carbon atoms or an aryl group having 6 to 50 carbon atoms; a benzofluorenyl group unsubstituted or substituted with an alkyl group having 1 to 50 carbon atoms; a phenanthrenyl group; an anthracenyl group; a dibenzofuranyl group unsubstituted or substituted with an alkyl group having 1 to 50 carbon atoms or a cycloalkyl group having 3 to 50 carbon atoms; a naphthobenzofuranyl group; a dibenzothiophene group unsubstituted or substituted with an alkyl group having 1 to 50 carbon atoms or a cycloalkyl group having 3 to 50 carbon atoms; a carbazolyl group unsubstituted or substituted with an alkyl group having 1 to 50 carbon atoms or an aryl group having 6 to 50 carbon atoms; a thiophene group unsubstituted or substituted with an alkyl group having 1 to 50 carbon atoms, an aryl group having 6 to 50 carbon atoms, a heteroaryl group having 2 to 50 carbon atoms or a substituent formed with two or more combinations thereof; a quinolyl group; an isoquinolyl group; a pyridazinyl group; a triazinyl group; a pyrimidinyl group; a pyridinyl group; a benzoxazolyl group; a benzothiazolyl group; a benzoxathiolyl group; a pyrenyl group; a fluoranthenyl group; a spirobifluorenyl group; a benzimidazolyl group unsubstituted or substituted with an alkyl group having 1 to 50 carbon atoms or an aryl group having 6 to 50 carbon atoms; a quinoxalinyl group; or a triphenylenyl group.

According to one embodiment of the present specification, $Ar_6$ and $Ar_7$ are the same as each other.

According to one embodiment of the present specification, $Ar_6$ and $Ar_7$ are different from each other.

According to one embodiment of the present specification, $Ar_6$ and $Ar_7$ are the same as or different from each other, and each independently a substituted or unsubstituted aryl group having 6 to 50 carbon atoms.

According to one embodiment of the present specification, $Ar_6$ and $Ar_7$ are the same as or different from each other, and each independently a phenyl group unsubstituted or substituted with an alkyl group having 1 to 50 carbon atoms, an aryl group having 6 to 50 carbon atoms, an alkoxy group having 1 to 50 carbon atoms, a halogen group, a cyano group, an alkylsilyl group having 1 to 50 carbon atoms, a heteroaryl group having 2 to 50 carbon atoms or a substituent formed with two or more combinations thereof; a biphenyl group unsubstituted or substituted with an alkyl group having 1 to 50 carbon atoms, a halogen group, a cyano group or an alkylsilyl group having 1 to 50 carbon atoms; a terphenyl group unsubstituted or substituted with an alkyl group having 1 to 50 carbon atoms, a halogen group, a cyano group or an alkylsilyl group having 1 to 50 carbon atoms; a naphthyl group unsubstituted or substituted with an alkyl group having 1 to 50 carbon atoms, a halogen group, a cyano group or an alkylsilyl group having 1 to 50 carbon atoms; or a fluorenyl group unsubstituted or substituted with an alkyl group having 1 to 50 carbon atoms, a halogen group, a cyano group, an alkylsilyl group having 1 to 50 carbon atoms or an aryl group having 6 to 50 carbon atoms.

According to one embodiment of the present specification, $Ar_6$ and $Ar_7$ are the same as or different from each other, and each independently a phenyl group unsubstituted or substituted with an alkyl group having 1 to 50 carbon atoms, an aryl group having 6 to 50 carbon atoms, an alkoxy group having 1 to 50 carbon atoms, a halogen group, a cyano group, an alkylsilyl group having 1 to 50 carbon atoms, a heteroaryl group having 2 to 50 carbon atoms or a substituent formed with two or more combinations thereof; a biphenyl group unsubstituted or substituted with an alkyl group having 1 to 50 carbon atoms, a halogen group, a cyano group or an alkylsilyl group having 1 to 50 carbon atoms; or a terphenyl group unsubstituted or substituted with an alkyl group having 1 to 50 carbon atoms, a halogen group, a cyano group or an alkylsilyl group having 1 to 50 carbon atoms.

According to one embodiment of the present specification, $Ar_6$ and $Ar_7$ are the same as or different from each other, and each independently a phenyl group; a biphenyl group; or a terphenyl group.

According to one embodiment of the present specification, $R_{100}$ is hydrogen; deuterium; a halogen group; a cyano group; a substituted or unsubstituted alkyl group having 1 to 50 carbon atoms; a substituted or unsubstituted cycloalkyl group having 3 to 50 carbon atoms; a substituted or unsubstituted alkoxy group having 1 to 50 carbon atoms; a substituted or unsubstituted aryloxy group having 6 to 50 carbon atoms; a substituted or unsubstituted alkenyl group having 2 to 50 carbon atoms; a substituted or unsubstituted silyl group; a substituted or unsubstituted amine group; a substituted or unsubstituted aryl group having 6 to 50 carbon atoms; or a substituted or unsubstituted heteroaryl group having 2 to 50 carbon atoms.

According to one embodiment of the present specification, $R_{100}$ is hydrogen; or a substituted or unsubstituted alkyl group having 1 to 50 carbon atoms.

According to one embodiment of the present specification, $R_{100}$ is hydrogen.

According to one embodiment of the present specification, $L_{11}$ to $L_{14}$ are the same as or different from each other, and each independently a direct bond; or a substituted or unsubstituted arylene group having 6 to 50 carbon atoms.

According to one embodiment of the present specification, $L_{11}$ to $L_{14}$ are the same as or different from each other, and each independently a direct bond; a substituted or unsubstituted phenylene group; or a substituted or unsubstituted naphthylene group.

According to one embodiment of the present specification, $L_{11}$ to $L_{14}$ are the same as or different from each other, and each independently a direct bond; a phenylene group; or a naphthylene group.

According to one embodiment of the present specification, $L_{12}$ and $L_{14}$ are the same as or different from each other, and each independently a direct bond; a phenylene group; or a naphthylene group.

According to one embodiment of the present specification, $L_{12}$ and $L_{14}$ are a direct bond.

According to one embodiment of the present specification, $L_{12}$ and $L_{14}$ are a phenylene group.

According to one embodiment of the present specification, $L_{11}$ and $L_{13}$ are the same as or different from each other, and each independently a direct bond; a phenylene group; or a naphthylene group.

According to one embodiment of the present specification, $Ar_{11}$ and $Ar_{13}$ are the same as or different from each other, and each independently a substituted or unsubstituted aryl group having 6 to 50 carbon atoms; or a substituted or unsubstituted heteroaryl group having 2 to 50 carbon atoms.

According to one embodiment of the present specification, $Ar_{11}$ and $Ar_{13}$ are the same as or different from each other, and each independently an aryl group having 6 to 50 carbon atoms unsubstituted or substituted with an aryl group having 6 to 50 carbon atoms or a heteroaryl group having 2 to 50 carbon atoms; or a heteroaryl group having 2 to 50 carbon atoms unsubstituted or substituted with an aryl group having 6 to 50 carbon atoms or a heteroaryl group having 2 to 50 carbon atoms.

According to one embodiment of the present specification, $Ar_{11}$ and $Ar_{13}$ are the same as or different from each other, and each independently a substituted or unsubstituted phenyl group; a substituted or unsubstituted biphenyl group; a substituted or unsubstituted naphthyl group; a substituted or unsubstituted thiophenyl group; a substituted or unsubstituted naphthobenzofuran group; or a substituted or unsubstituted indolocarbazole group.

According to one embodiment of the present specification, $Ar_{11}$ and $Ar_{13}$ are the same as or different from each other, and each independently a phenyl group unsubstituted or substituted with an aryl group, a heteroaryl group or a substituent formed with two or more combinations thereof; a biphenyl group; a naphthyl group unsubstituted or substituted with an aryl group; a thiophenyl group unsubstituted or substituted with an aryl group; a naphthobenzofuran group; or an indolocarbazole group.

According to one embodiment of the present specification, $Ar_{11}$ and $Ar_{13}$ are the same as or different from each other, and each independently a phenyl group unsubstituted or substituted with an aryl group; a biphenyl group; a naphthyl group unsubstituted or substituted with an aryl group; a thiophenyl group unsubstituted or substituted with an aryl group; a naphthobenzofuran group; or an indolocarbazole group.

According to one embodiment of the present specification, $Ar_{11}$ and $Ar_{13}$ are the same as or different from each other, and each independently a substituted or unsubstituted aryl group having 6 to 50 carbon atoms.

According to one embodiment of the present specification, $Ar_{11}$ and $Ar_{13}$ are the same as or different from each other, and each independently a substituted or unsubstituted phenyl group; a substituted or unsubstituted biphenyl group; or a substituted or unsubstituted naphthyl group.

According to one embodiment of the present specification, $Ar_{11}$ and $Ar_{13}$ are the same as or different from each other, and each independently a phenyl group unsubstituted or substituted with an aryl group; a biphenyl group; or a naphthyl group unsubstituted or substituted with an aryl group.

According to one embodiment of the present specification, $Ar_{11}$ and $Ar_{13}$ are the same as or different from each other, and each independently a phenyl group; a biphenyl group; or a naphthyl group.

According to one embodiment of the present specification, $Ar_{12}$ and $Ar_{14}$ are the same as or different from each other, and each independently a hydrogen; deuterium; a halogen group; a cyano group; a substituted or unsubstituted alkyl group; a substituted or unsubstituted aryl group; or a substituted or unsubstituted heteroaryl group.

According to one embodiment of the present specification, $Ar_{12}$ and $Ar_{14}$ are hydrogen.

According to one embodiment of the present specification, Chemical Formula 3 may be represented by the following Chemical Formula 7 or 10.

[Chemical Formula 7]

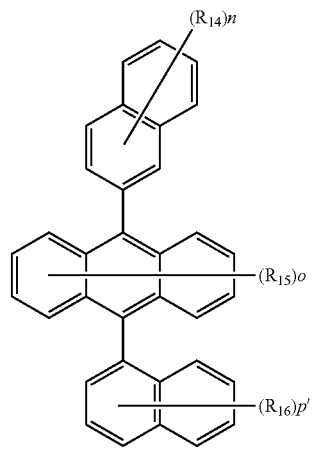

[Chemical Formula 10]

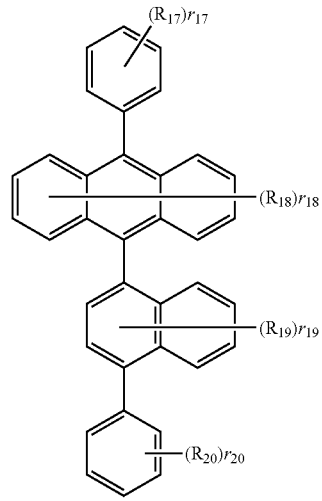

In Chemical Formulae 7 and 10, $R_{14}$ to $R_{20}$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, $r_{17}$ and $r_{20}$ are an integer of 1 to 5, $r_{19}$ g is an integer of 1 to 6, n and p' are an integer of 1 to 7, o and $r_{18}$ are an integer of 1 to 8, and when $r_{17}$ to $r_{20}$, n, o and p' are 2 or greater, substituents in the parentheses are the same as or different from each other.

According to one embodiment of the present specification, $R_{14}$ to $R_{20}$ are hydrogen.

According to one embodiment of the present specification, Chemical Formula 1 may be represented by the following Chemical Formula 8.

[Chemical Formula 8]

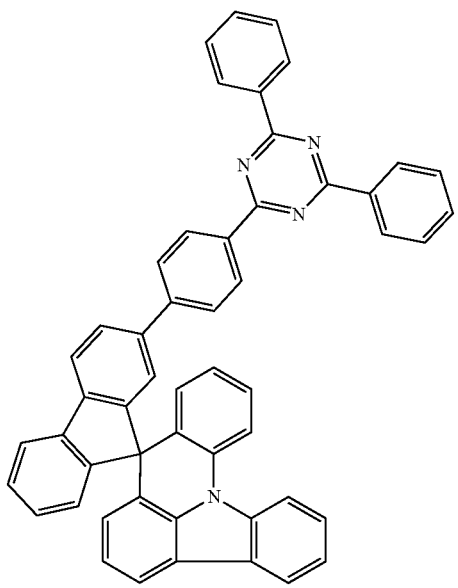

According to one embodiment of the present specification, Chemical Formula 3 may be represented by the following Chemical Formula 9 or 11.

[Chemical Formula 9]

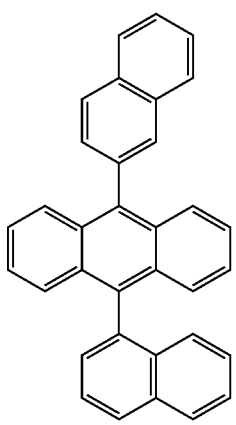

[Chemical Formula 11]

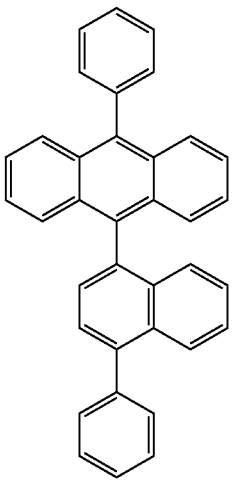

According to one embodiment of the present specification, the compounds of Chemical Formulae 1 to 3 may be prepared as in the following preparation examples, however, the preparation is not limited thereto. In the following preparation examples, types and the number of substituents may be determined by those skilled in the art properly selecting known starting materials. As reaction types and reaction conditions, those known in the art may be used.

One embodiment of the present specification provides an organic electroluminescent device comprising a first electrode; a second electrode; and one or more organic material layers provided between the first electrode and the second electrode, wherein the organic material layer comprises the light emitting layer and the electron transfer layer described above.

According to one embodiment of the present specification, the organic material layer may further comprise one or more layers selected from the group consisting of a hole injection layer, a hole transfer layer, a light emitting layer, an electron transfer layer and an electron injection layer.

For example, the organic electroluminescent device of the present disclosure may have a structure comprising a hole injection layer, a hole transfer layer, an electron blocking layer, a light emitting layer, a hole blocking layer, an electron transfer layer, an electron injection layer and the like as the organic material layer. However, the structure of the organic electroluminescent device is not limited thereto, and may comprise less or more numbers of organic material layers.

For example, the organic electroluminescent device of the present specification may have structures as illustrated in FIG. 1 and FIG. 2, however, the structure is not limited thereto.

FIG. 1 illustrates a structure of the organic electroluminescent device (10) in which a first electrode (30), a light emitting layer (40), an electron transfer layer (80) and a second electrode (50) are consecutively laminated on a substrate (20). FIG. 1 is an exemplary structure of the organic electroluminescent device according to one embodiment of the present specification, and the structure may further comprise other organic material layers.

FIG. 2 illustrates a structure of the organic electroluminescent device (11) in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of the organic electroluminescent device according to one embodiment of the present specification, and the structure may further comprise other organic material layers.

The organic electroluminescent device according to one embodiment of the present specification comprises a first electrode; a second electrode; and an organic material layer provided between the first electrode and the second electrode, wherein the organic material layer comprises a light emitting layer and an electron transfer layer, the light emitting layer comprises a first host material, a second host material and a dopant material, the first host material has a HOMO energy level of −5.9 eV or lower, and the second host material may have a HOMO energy level higher than a HOMO energy level of the first host material by 0.1 eV to 0.2 eV.

The organic electroluminescent device according to one embodiment of the present specification comprises a first electrode; a second electrode; and a light emitting layer and an electron transfer layer between the first electrode and the second electrode, wherein one or more layers of an electron blocking layer, a hole transfer layer and a hole injection layer may be provided between the light emitting layer and the first electrode.

The organic electroluminescent device according to one embodiment of the present specification comprises a first electrode; a second electrode; and a light emitting layer between the first electrode and the second electrode, wherein an electron transfer layer is provided between the light emitting layer and the second electrode, and one or more layers of an electron blocking layer, a hole transfer layer and a hole injection layer may be provided between the light emitting layer and the first electrode.

The organic electroluminescent device according to one embodiment of the present specification comprises a first electrode; a second electrode; and a light emitting layer between the first electrode and the second electrode, wherein an electron transfer layer is provided between the light emitting layer and the second electrode, an electron blocking layer is provided between the light emitting layer and the first electrode, and one or more layers of a hole transfer layer and a hole injection layer may be provided between the electron blocking layer and the first electrode.

The organic electroluminescent device according to one embodiment of the present specification comprises a first electrode; a second electrode; and a light emitting layer between the first electrode and the second electrode, wherein an electron transfer layer is provided between the light emitting layer and the second electrode, an electron blocking layer is provided between the light emitting layer and the first electrode, a hole transfer layer is provided between the electron blocking layer and the first electrode, and a hole injection layer may be provided between the hole transfer layer and the first electrode.

According to one embodiment of the present specification, the electron transfer layer may be a layer carrying out electron injection and electron transfer at the same time.

In other words, the layer carrying out electron injection and electron transfer at the same time may comprise the compound represented by Chemical Formula 1 or Chemical Formula 2.

According to one embodiment of the present specification, the light emitting layer is a blue light emitting layer.

According to one embodiment of the present specification, the organic material layer comprises a light emitting layer, the light emitting layer comprises a first host material and a second host material, and the first host material and the second host material are different from each other.

According to one embodiment of the present specification, the light emitting layer comprises a first host material and a second host material, and at least one of the first host material and the second host material comprises the compound represented by Chemical Formula 3.

According to one embodiment of the present specification, the light emitting layer comprises a first host material and a second host material, and the first host material and the second host material each independently comprise the compound represented by Chemical Formula 3.

According to one embodiment of the present specification, the light emitting layer comprises a first host material and a second host material, the first host material and the second host material are different from each other, and the first host material and the second host material each independently comprise the compound represented by Chemical Formula 3.

According to one embodiment of the present specification, the organic material layer comprises a light emitting layer, the light emitting layer comprises a dopant material, and the dopant material comprises a pyrene-based dopant material.

According to one embodiment of the present specification, the organic material layer comprises a light emitting layer, the light emitting layer comprises a first host material, a second host material and a dopant material, the first host material and the second host material comprises the compound represented by Chemical Formula 3, and the dopant material comprises a pyrene-based dopant material.

According to one embodiment of the present specification, the organic material layer comprises a light emitting layer, the light emitting layer comprises a first host material, a second host material and a dopant material, the first host material and the second host material comprise the compound represented by Chemical Formula 3, the dopant material comprises a pyrene-based dopant material, and the pyrene-based material may be a pyrene-based dopant material of PL Max 452 nm.

A photoluminescence (PL) Max 452 nm spectrum of the pyrene-based dopant material capable of being used in one embodiment of the present specification is presented in FIG. 3.

The organic electroluminescent device of the present specification may be manufactured using materials and methods known in the art, except that one or more layers of the organic material layers include the compound of the present specification, that is, one, two or more types of compounds selected from among the compounds represented by Chemical Formulae 1 to 3.

When the organic electroluminescent device comprises a plurality of the organic material layers, the organic material layers may be formed with materials the same as or different from each other.

For example, the organic electroluminescent device of the present specification may be manufactured by consecutively laminating a first electrode, an organic material layer and a second electrode on a substrate. Herein, the organic electroluminescent device may be manufactured by forming a first electrode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer thereon, and then depositing a material capable of being used as a second electrode thereon. In addition to such a method, the organic electroluminescent device may also be manufactured by consecutively depositing a second electrode material, an organic material layer and a first electrode material on a substrate.

In addition, the organic material layer may be formed using a solution coating method as well as a vacuum deposition method when manufacturing the organic electroluminescent device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material.

The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The organic electroluminescent device according to the present specification may be a top-emission type, a bottom-emission type or a dual-emission type depending on the materials used.

Hereinafter, the present specification will be described in detail with reference to examples. However, the examples according to the present specification may be modified to various different forms, and the scope of the present specification is not to be construed as being limited to the examples described below. Examples of the present specification are provided in order to more fully describe the present specification to those having average knowledge in the art.

SYNTHESIS EXAMPLE

Preparation Example 1

Synthesis of Compound P1

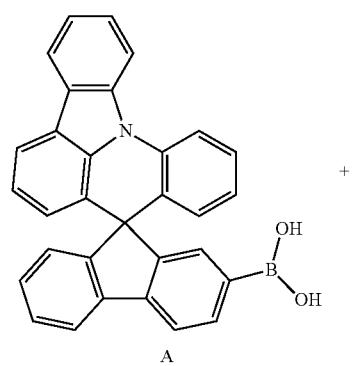

A

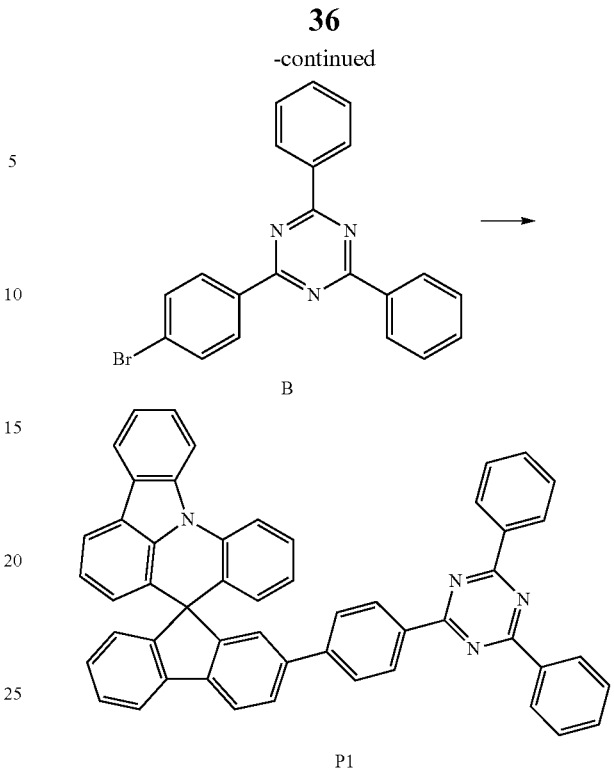

B

P1

After completely dissolving Compound A and Compound B (8.64 g, 22.3 mmol) in THF (100 mL), potassium carbonate (9.3 g, 66.8 mmol) dissolved in 50 mL of water was added thereto. After introducing tetrakistriphenyl-phosphino palladium (772 mg, 0.67 mmol) thereto, the result was heated and stirred for 8 hours. After lowering the temperature to room temperature and terminating the reaction, the potassium carbonate solution was removed to filter white solids. The filtered white solids were washed twice each with THF and ethyl acetate to prepare Compound P1 (14.1 g, yield 89%).

MS [M+H]$^+$ (Compound P1)=713

Preparation Example 2

Synthesis of Compound P2

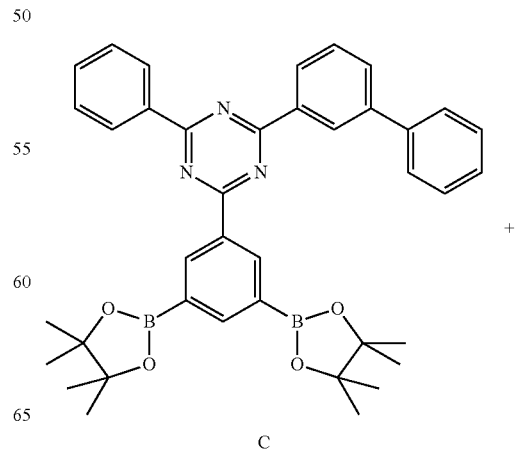

C

-continued

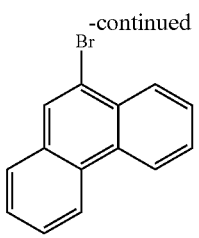

D

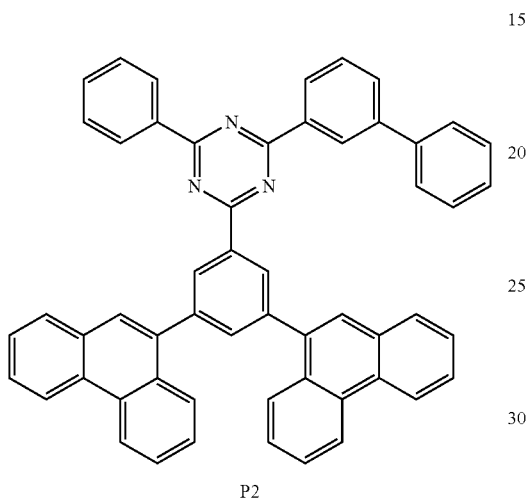

P2

After completely dissolving Compound C (20 g, 31.4 mmol) and Compound D (9-bromophenanthrene) (20.2 g, 78.5 mmol) in 200 mL of a tetrahydrofuran (THF) solvent, potassium carbonate ($K_2CO_3$) dissolved in water (80 mL) was added thereto. After introducing tetrakistriphenyl-phosphino palladium (1.1 g, 0.94 mmol) thereto, the result was heated and stirred for 6 hours. After verifying that the reaction was progressed, the temperature was lowered to room temperature and the reaction was terminated. After removing the potassium carbonate solution and filtering solids, the filtered solids were washed with ethyl acetate and ethanol to prepare Compound P2 (20 g, yield 86.4%).

MS $[M+H]^+$ (Compound P2)=738

Preparation Example 3

Synthesis of Compound G and Compound P3

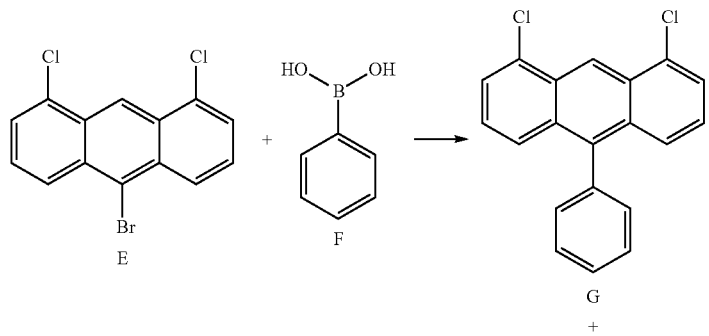

E + F → G +

-continued

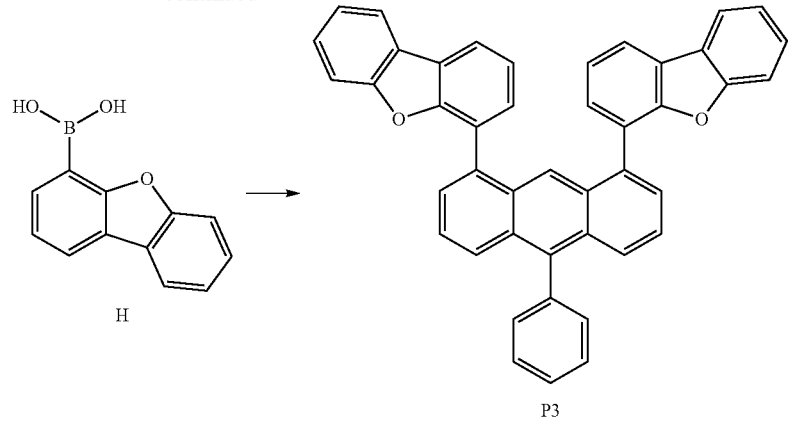

After synthesizing Compound G using Compound E and Compound F, Compound P3 was prepared in the same manner as in Preparation Example 1 except that Compound H was used instead of Compound A and Compound G was used instead of Compound B.
MS [M+H]$^+$ (Compound G)=322
MS [M+H]$^+$ (Compound P3)=586

Preparation Example 4

Synthesis of Compound P4

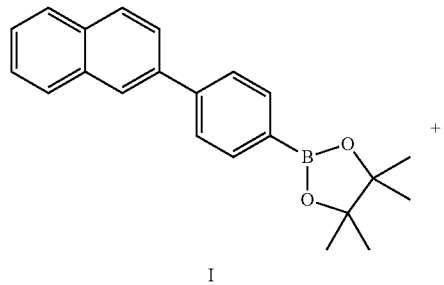

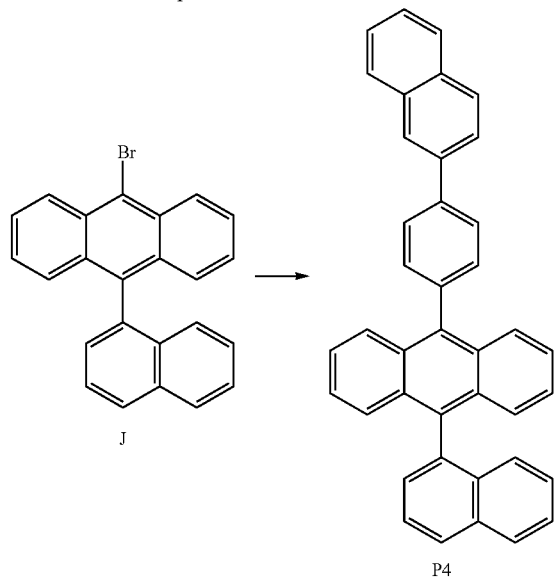

Compound P4 was prepared in the same manner as in Preparation Example 1 except that Compound I was used instead of Compound A and Compound J was used instead of Compound B.
MS [M+H]$^+$ (Compound P4)=507

Preparation Example 5

Synthesis of Compound P5

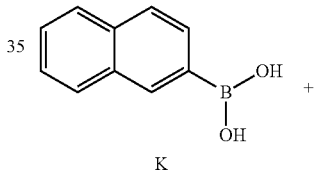

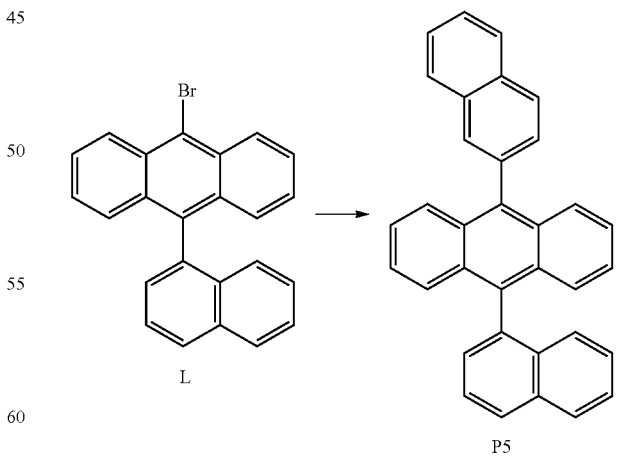

Compound P5 was prepared in the same manner as in Preparation Example 1 except that Compound K was used instead of Compound A and Compound L was used instead of Compound B.

MS [M+H]+ (Compound P5)=431

Preparation Example 6

Synthesis of Compound P6

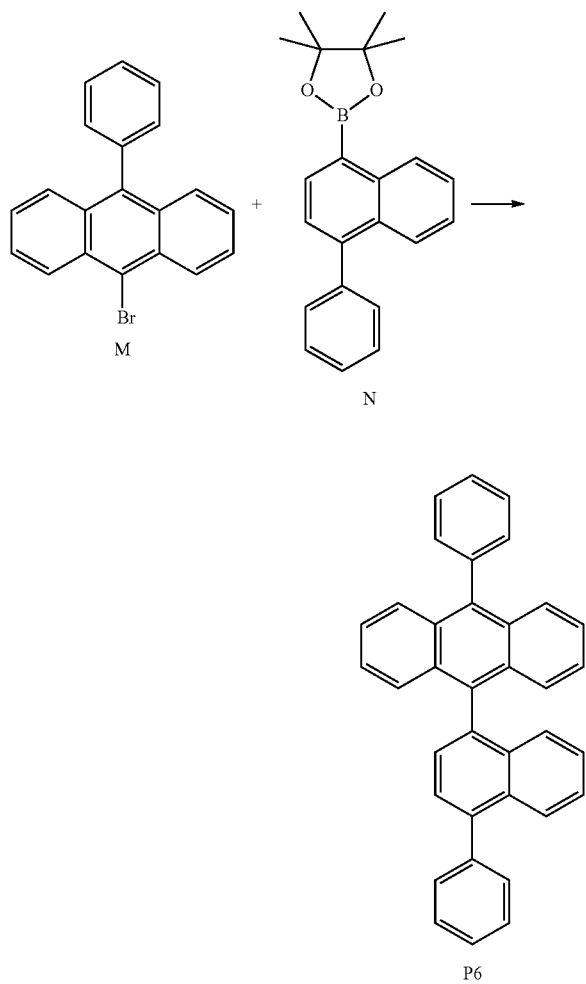

Using a 0.5 L flask, Compound M (30.0 g, 0.09 mol) and Compound N (32.7 g, 0.10 mol) were dissolved in 0.3 L of tetrahydrofuran (THF) under nitrogen, and then a solution dissolving potassium carbonate (37.3 g, 0.27 mol) in 0.1 L of distilled water was introduced thereto. After that, tetrakis (triphenylphosphine)palladium (5.20 g, 0.0045 mol) was introduced thereto, the temperature was raised, and the result was stirred under reflux for 3 hours. After completing the reaction, the result was cooled to room temperature, and extracted with toluene and water. The organic layer was taken, treated with anhydrous magnesium sulfate and active carbon, and then filtered using a celite pad. The filtrate was vacuum concentrated, and purified through recrystallization with toluene and ethyl alcohol to obtain Compound P6 (32 g, 78% yield).

MS [M+H]+ (Compound P6)=457

Synthesis identification materials (MS) are shown in the following Table 1.

TABLE 1

| Compound | MS [M + H]+ |
|---|---|
| Compound P1 | 713 |
| Compound P2 | 738 |
| Compound G | 322 |
| Compound P3 | 586 |
| Compound P4 | 507 |
| Compound P5 | 431 |
| Compound P6 | 457 |

Example 1

A glass substrate on which indium tin oxide (ITO) was coated as a thin film to a thickness of 1,300 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 1 minute using nitrogen plasma, and then transferred to a vacuum depositor.

On the transparent ITO electrode prepared as above, a hole injection layer was formed by thermal vacuum depositing hexanitrile hexaazatriphenylene (HAT) to a thickness of 500 Å.

A hole transfer layer was formed on the hole injection layer by vacuum depositing 4-4'-bis[N-(1-naphthyl)-N-phenylamino]biphenyl (NPB) (300 Å), a material transferring holes.

Subsequently, an electron blocking layer was formed on the hole transfer layer to a film thickness of 100 Å by vacuum depositing the following TCTA.

Subsequently, a light emitting layer was formed on the electron blocking layer to a film thickness of 200 Å by vacuum depositing Compound P4 synthesized in Preparation Example 4 and Compound P5 synthesized in Preparation Example 5 as a host, and a pyrene-based dopant of PL Max 452 nm.

On the light emitting layer, an electron injection and transfer layer was formed to a thickness of 300 Å by vacuum depositing Compound P1 synthesized in Preparation Example 1. A cathode was formed on the electron injection and transfer layer by depositing lithium fluoride (LiF) to a thickness of 10 Å and aluminum to a thickness of 1,000 Å in consecutive order.

An organic electroluminescent device was manufactured by maintaining, in the above-mentioned processes, the deposition rates of the organic materials at 0.4 Å/sec to 1 Å/sec, the deposition rates of the lithium fluoride and the aluminum of the cathode at 0.5 Å/sec and 2 Å/sec, respectively, and the degree of vacuum during the deposition at $5 \times 10^{-8}$ torr to $8 \times 10^{-8}$ torr.

Example 2

An organic electroluminescent device was manufactured in the same manner as in Example 1 except that Compound P6 and Compound P5 were used as the host material.

Comparative Example 1

An organic electroluminescent device was manufactured in the same manner as in Example 1 except that only Compound P5 was used as the host material.

Comparative Example 2

An organic electroluminescent device was manufactured in the same manner as in Example 1 except that only Compound P3 was used as the host material.

Comparative Example 3

An organic electroluminescent device was manufactured in the same manner as in Example 1 except that only Compound P4 was used as the host material.

Comparative Example 4

An organic electroluminescent device was manufactured in the same manner as in Example 1 except that Compound P3 and Compound P5 were used as the host material.

[HAT]

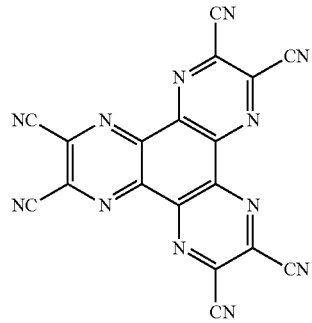

[NPB]

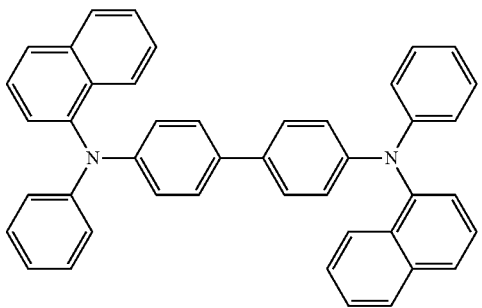

[TCTA]

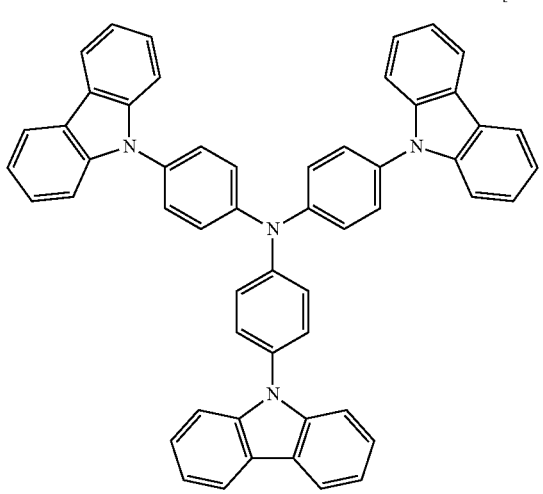

Driving voltage, current efficiency (cd/A), power efficiency (QE), luminance (CIE-x, CIE-y) and lifetime of the organic electroluminescent devices manufactured in Examples 1 and 2 and Comparative Examples 1 to 4 are shown in the following Table 2.

TABLE 2

| Category | | HOMO (eV) | Voltage-Current-Luminance | | | | | Lifetime @ 95%, DC 20 mA/cm² |
|---|---|---|---|---|---|---|---|---|
| | | | Voltage (V) | cd/A | QE (%) | CIE-x | CIE-y | |
| Comparative Example 1 | Compound P5 | −5.95 | 4.0 | 8.0 | 10.4 | 0.136 | 0.095 | 157.2 |
| Comparative Example 2 | Compound P3 | −5.65 | 3.6 | 7.9 | 8.8 | 0.138 | 0.115 | 80.1 |
| Comparative Example 3 | Compound P4 | −5.82 | 3.9 | 7.9 | 10.2 | 0.138 | 0.094 | 220.0 |
| Comparative Example 4 | Compound P3 | −5.65 | 3.8 | 8.4 | 10.0 | 0.138 | 0.104 | 182.2 |
| | Compound P5 | −5.95 | | | | | | |
| Example 1 | Compound P4 | −5.82 | 3.8 | 8.0 | 10.4 | 0.138 | 0.093 | 250.0 |
| | Compound P5 | −5.95 | | | | | | |
| Example 2 | Compound P6 | −5.84 | 3.8 | 8.61 | 10.74 | 0.138 | 0.098 | 243.0 |
| | Compound P5 | −5.95 | | | | | | |

According to Table 2, it was identified that the blue organic electroluminescent devices of Examples 1 and 2 using two types of host materials had excellent driving voltage and/or current efficiency, and particularly, exhibited more superior performance in terms of a lifetime, compared to the blue organic electroluminescent devices of Comparative Examples 1 to 3 using one type of host material.

In addition, it was identified that the blue organic electroluminescent devices of Example 1 in which two types of host materials included in the light emitting layer had a HOMO energy level difference of 0.13 eV and Example 2 in which the difference was 0.11 eV exhibited a significantly superior effect in terms of a lifetime while having similar driving voltage and current efficiency, compared to the blue organic electroluminescent device of Comparative Example 4 using two types of host materials having a HOMO energy level difference of Δ0.2 eV or greater.

Particularly, when comparing Examples 1 and 2 and Comparative Example 1, it was identified that Example 1, in which the first host material according to one embodiment of the present specification had a HOMO energy level of −5.9 eV or lower and the second host material had a HOMO energy level higher than a HOMO energy level of the first host material by 0.1 eV to 0.2 eV, had a decreased driving voltage, and improved current efficiency, power efficiency and lifetime compared to Comparative Example 1 using a host material having a HOMO energy level of −5.9 eV or lower alone.

Hereinbefore, preferred embodiments of the present specification have been described, however, the present disclosure is not limited thereto, and various modifications may be made within the scope of the claims and the detailed descriptions of the disclosure, and the modifications are also included in the scope of the present disclosure.

The invention claimed is:

1. An organic electroluminescent device comprising:
a first electrode;
a second electrode; and
an organic material layer provided between the first electrode and the second electrode,
wherein the organic material layer comprises a light emitting layer and an electron transfer layer,
the light emitting layer comprises a first host material, a second host material and a dopant material,
the first host material has a HOMO energy level of −5.9 eV or lower,
the second host material has a HOMO energy level higher than a HOMO energy level of the first host material by 0.1 eV to 0.2 eV, and
wherein the dopant material is a pyrene-based dopant material.

2. The organic electroluminescent device of claim 1, wherein the light emitting layer is a blue light emitting layer.

3. The organic electroluminescent device of claim 1, wherein the electron transfer layer comprises a compound having a structure of an electron donor and an electron acceptor bonding to each other.

4. The organic electroluminescent device of claim 1, wherein the electron transfer layer comprises a compound represented by the following Chemical Formula 1 or Chemical Formula 2:

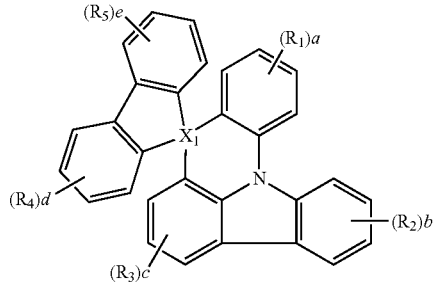

[Chemical Formula 1]

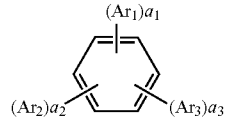

[Chemical Formula 2]

in Chemical Formulae 1 and 2, $X_1$ is C or Si;

at least one of $R_1$ to $R_5$ is each independently represented by $-(L_i)z_1-A_1$;

at least one of $Ar_1$ to $Ar_3$ is each independently represented by $-(L_2)z_2-A_2$;

$a_1$ to $a_3$ are the same as or different from each other, and each independently an integer of 1 to 4, $a_1+a_2+a_3 \leq 6$, and when $a_1$ to $a_3$ are an integer of 2 or greater, substituents in the parentheses are the same as or different from each other;

$L_1$ and $L_2$ are the same as or different from each other, and each independently a direct bond; or a divalent group comprising one or more types selected from the group consisting of a substituted or unsubstituted arylene group and a substituted or unsubstituted heteroarylene group, $z_1$ and $z_2$ are an integer of 1 or 2, and when $z_1$ and $z_2$ are 2, substituents in the parentheses are the same as or different from each other;

$A_1$ and $A_2$ are the same as or different from each other, and each independently a substituted or unsubstituted aryl group; or a substituted or unsubstituted heteroaryl group comprising one or more Ns; and the rest of $R_1$ to $R_5$ that are not $-(Li)z_1-A_1$ and the rest of $Ar_1$ to $Ar_3$ that are not $-(La)z_2-A_2$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, a, b, d and e are the same as or different from each other and each independently an integer of 1 to 4, c is an integer of 1 to 3, and when a to e are each 2 or greater, substituents in the parentheses are the same as or different from each other.

5. The organic electroluminescent device of claim 1, wherein at least one of the first host material and the second host material is represented by a compound of the following Chemical Formula 3:

[Chemical Formula 3]

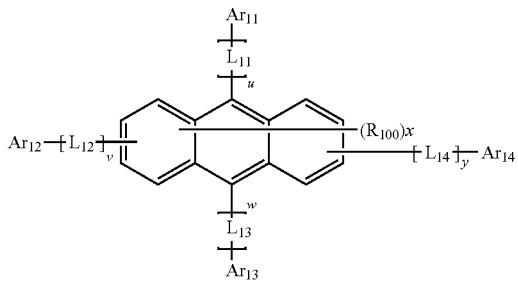

in Chemical Formula 3, $R_{100}$ is hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroaryl group, x is an integer of 1 to 6, and when x is 2 or greater, $R_{100}$s are the same as or different from each other;

$L_{11}$ to $L_{14}$ are the same as or different from each other, and each independently a direct bond; or a substituted or unsubstituted arylene group, u, v, w and y are each an integer of 1 or 2, and when y is 2, $L_{11}$s are the same as or different from each other, when v is 2, $L_{12}$s are the same as or different from each other, when w is 2, $L_{13}$s are the same as or different from each other, and when y is 2, $L_{14}$s are the same as or different from each other;

$Ar_{11}$ and $Ar_{13}$ are the same as or different from each other, and each independently a substituted or unsubstituted aryl group; or a substituted or unsubstituted heteroaryl group; and $Ar_{12}$ and $Ar_{14}$ are the same as or different from each other, and each independently hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroaryl group.

6. The organic electroluminescent device of claim 4, wherein Ai is a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted oxazole group; a substituted or unsubstituted isoxazole group; a substituted or unsubstituted thiazole group; a substituted or unsubstituted triazole group; a substituted or unsubstituted isothiazole group; a substituted or unsubstituted oxadiazole group; a substituted or unsubstituted thiadiazole group; a substituted or unsubstituted dithiazole group; a substituted or unsubstituted tetrazole group; a substituted or unsubstituted diazine group; a substituted or unsubstituted oxazine group; a substituted or unsubstituted triazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzothiazole group; a substituted or unsubstituted benzoxazole group; a substituted or unsubstituted benzimidazole group; a substituted or unsubstituted carbazole group; a substituted or unsubstituted benzocarbazole group; a substituted or unsubstituted phenazine group; or a substituted or unsubstituted phenoxazine group.

7. The organic electroluminescent device of claim 4, wherein $A_2$ is a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted perylenyl group; a substituted or unsubstituted fluoranthenyl group; a substituted or unsubstituted triphenylenyl group; a substituted or unsubstituted phenalenyl group; a substituted or unsubstituted chrysenyl group; a substituted or unsubstituted fluorenyl group; a substituted or unsubstituted benzofluorenyl group; a substituted or unsubstituted spirobifluorenyl group; a substituted or unsubstituted triphenylene group; a substituted or unsubstituted spirobenzoanthracenefluorenyl group; a substituted or unsubstituted pyridine group; a substituted or unsubstituted pyrrole group; a substituted or unsubstituted pyrimidine group; a substituted or unsubstituted pyridazine group; a substituted or unsubstituted imidazole group; a substituted or unsubstituted pyrazole group; a substituted or unsubstituted oxazole group; a substituted or unsubstituted isoxazole group; a substituted or unsubstituted thiazole group; a substituted or unsubstituted triazole group; a substituted or unsubstituted oxadiazole group; a substituted or unsubstituted thiadiazole group; a substituted or unsubstituted dithiazole group; a substituted or unsubstituted tetrazole group; a substituted or unsubstituted diazine group; a substituted or unsubstituted oxazine group; a substituted or unsubstituted triazine group; a substituted or unsubstituted isoquinoline group; a substituted or unsubstituted quinoline group; a substituted or unsubstituted quinol group; a substituted or unsubstituted quinazoline group; a substituted or unsubstituted quinoxaline group; a substituted or unsubstituted acridine group; a substituted or unsubstituted phenanthridine group; a substituted or unsubstituted diazanaphthalene group; a substituted or unsubstituted indole group; a substituted or unsubstituted benzothiazole group; a substituted or unsubstituted benzoxazole group; a substituted or unsubstituted benzimidazole group; a substituted or unsubstituted carbazole group; a substituted or unsubstituted benzocarbazole group; a substituted or unsubstituted phenazine group; or a substituted or unsubstituted phenoxazine group.

8. The organic electroluminescent device of claim 4, wherein Chemical Formula 1 is represented by the following Chemical Formula 4:

[Chemical Formula 4]

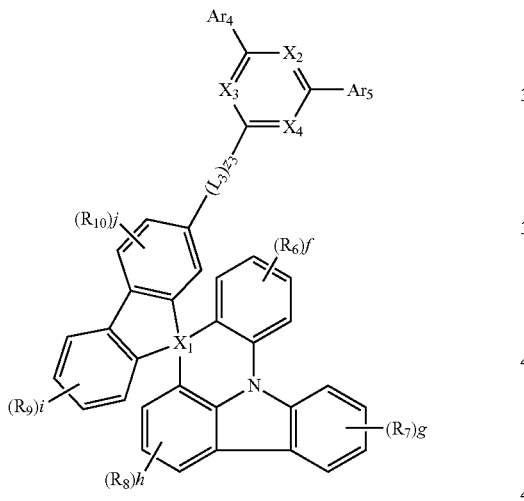

in Chemical Formula 4, $X_2$ to $X_4$ are the same as or different from each other, and each independently CR; or N, and at least one of $X_2$ to $X_4$ is N;

$Ar_4$ and $Ar_5$ are the same as or different from each other, and each independently a substituted or unsubstituted aryl group; or a substituted or unsubstituted heteroaryl group;

$L_3$ is a direct bond; or a divalent group comprising one or more types selected from the group consisting of a substituted or unsubstituted arylene group and a substituted or unsubstituted heteroarylene group, $z_3$ is an integer of 1 or 2, and when $z_3$ is 2, $L_3$s are the same as or different from each other;

R and $R_6$ to $R_{10}$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, f, g and i are the same as or different from each other and each independently an integer of 1 to 4, h and j are the same as or different from each other and each independently an integer of 1 to 3, and when f to j are each 2 or greater, substituents in the parentheses are the same as or different from each other; and the rest of the substituents have the same definitions as in Chemical Formula 1.

9. The organic electroluminescent device of claim 4, wherein Chemical Formula 2 is represented by the following Chemical Formula 5 or Chemical Formula 6:

[Chemical Formula 5]

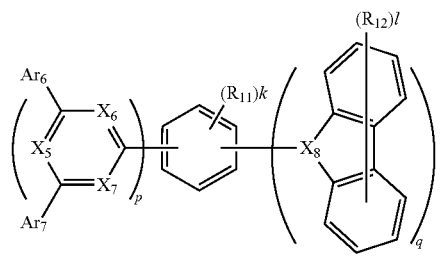

[Chemical Formula 6]

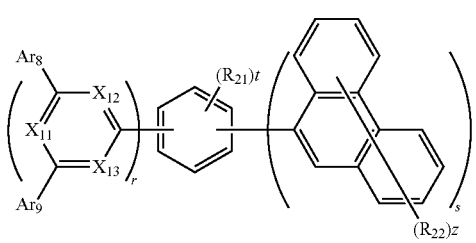

in Chemical Formulae 5 and 6, $X_5$ to $X_8$ and $X_{11}$ to $X_{13}$ are the same as or different from each other, and each independently CR'; or N, at least one of $X_5$ to $X_7$ is N, and at least one of $X_{11}$ to $X_{13}$ is N;

$Ar_6$ to $Ar_9$ are the same as or different from each other, and each independently a substituted or unsubstituted aryl group; or a substituted or unsubstituted heteroaryl group;

R' and $R_{11}$, $R_{12}$, $R_{21}$ and $R_{22}$ are the same as or different from each other, and each independently selected from the group consisting of hydrogen; deuterium; a halogen group; a cyano group; a nitro group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heteroaryl group, k and t are the same as or different from each other and each independently an integer of 1 to 4, l is an integer of 1 to 8, z is an integer of 1 to 9, p and r are the same as or different from each other and each independently an integer of 1 or greater, q and s are the same as or different from each other and each independently an integer of 1 or greater, $p+q+k \leq 6$, $t+r+s \leq 6$, and when k, l, p, q, r, s, t and z are each 2 or greater, substituents in the parentheses are the same as or different from each other.

10. The organic electroluminescent device of claim 5, wherein $Ar_{11}$ and $Ar_{13}$ are the same as or different from each other, and each independently a substituted or unsubstituted aryl group having 6 to 50 carbon atoms.

11. The organic electroluminescent device of claim 5, wherein $Ar_{11}$ and $Ar_{13}$ are the same as or different from each other, and each independently a substituted or unsubstituted phenyl group; a substituted or unsubstituted biphenyl group; or a substituted or unsubstituted naphthyl group.

12. The organic electroluminescent device of claim 1, wherein the organic material layer further comprises a hole injection layer, a hole transfer layer or an electron blocking layer.

13. The organic electroluminescent device of claim 1, wherein the organic material layer further comprises a hole blocking layer or an electron injection layer.

* * * * *